(12) United States Patent
Daubresse et al.

(10) Patent No.: US 7,407,517 B2
(45) Date of Patent: Aug. 5, 2008

(54) CATIONIC AZO DYES WITH JULOLIDINE UNITS, DYEING COMPOSITION CONTAINING THEM, METHOD OF DYEING

(75) Inventors: Nicolas Daubresse, La Celle Saint-Cloud (FR); Andrew Greaves, Montevrain (FR)

(73) Assignee: L'Oreal S.A., Paris (FR)

( * ) Notice: Subject to any disclaimer, the term of this patent is extended or adjusted under 35 U.S.C. 154(b) by 168 days.

(21) Appl. No.: 11/508,272

(22) Filed: Aug. 23, 2006

(65) Prior Publication Data

US 2007/0044250 A1 Mar. 1, 2007

(30) Foreign Application Priority Data

Aug. 23, 2005 (FR) .................................. 05 08695

(51) Int. Cl.
*A61Q 5/10* (2006.01)
*C07C 245/00* (2006.01)

(52) U.S. Cl. .................. 8/405; 8/406; 8/407; 8/408; 8/423; 8/435; 8/688; 8/689; 8/690; 8/691; 8/692; 534/575

(58) Field of Classification Search ............ 8/405, 8/406, 407, 408, 423, 435, 688, 689, 690, 8/691, 692; 534/575
See application file for complete search history.

(56) References Cited

U.S. PATENT DOCUMENTS

| | | | |
|---|---|---|---|
| RE30,199 E | | 1/1980 | Rose et al. |
| 4,341,853 A | * | 7/1982 | Horie et al. ............... 430/83 |
| 4,461,821 A | | 7/1984 | Sano et al. |
| 4,823,985 A | | 4/1989 | Grollier et al. |
| 5,061,289 A | | 10/1991 | Clausen et al. |
| 5,380,340 A | | 1/1995 | Neunhoeffer et al. |
| 5,534,267 A | | 7/1996 | Neunhoeffer et al. |
| 5,663,366 A | | 9/1997 | Neunhoeffer et al. |
| 5,708,151 A | | 1/1998 | Möckli |
| 5,766,576 A | | 6/1998 | Löwe et al. |
| 6,284,003 B1 | | 9/2001 | Rose et al. |
| 6,645,258 B2 | | 11/2003 | Vidal et al. |
| 6,730,789 B1 | | 5/2004 | Birault et al. |
| 2004/0237215 A1 | | 12/2004 | Gourlaouen |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| EP | 0 714 954 | 6/1996 |
| EP | 0 770 375 | 11/1997 |
| FR | 2 387 277 | 11/1978 |
| FR | 2 586 913 | 3/1987 |
| FR | 2 733 749 | 11/1996 |
| FR | 2 801 308 | 5/2001 |
| GB | 1 026 978 | 4/1966 |
| GB | 1 153 196 | 5/1969 |
| JP | 61-107251 | 5/1986 |
| JP | 2-19576 | 1/1990 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 03/060015 | 7/2003 |

OTHER PUBLICATIONS

STIC Search Report dated Mar. 14, 2008.*
French Search Report for FR 05/08695, dated Apr. 12, 2006.
English language Derwent Abstract of EP 0 770 375, Nov. 19, 1997.
English language Derwent Abstract of FR 2 387 277, Nov. 10, 1978.
English language Derwent Abstract of JP 61-107251, May 26, 1986.
English language Derwent Abstract of JP 2-19576, Jan. 23, 1990.
Deady, L. "Ring Nitrogen Oxidation of Amino Substituted Nitrogen Heterocycles with m-Chloroperbenzoic Acid", Synthetic Communications, 7 (8), 1977, pp. 509-514.
Hunig, S., "Heterocyclic Azo Dyes by Oxidative Coupling", Agnew Chem. Internat. Edit., vol. 1, No. 12, 1962, pp. 640-646.
Klein, J. et al., "Synthesis and Structure-Activity Relationships of N-Propyl-N-(4-pyridinyl)-1H-indol-1-amine (Besipirdine) and Related Analogs as Potential Therapeutic Agents for Alzheimer's Disease", J. Med. Chem., 1996, 39, pp. 570-581.
Smith M. et al., March's Advanced organic Chemistry: Reactions, Mechanisms, and Structure, 5$^{th}$ Edit., John Wiley & Sons, 2001.
Venkataraman, K., The Chemistry of Synthetic Dyes, vol. II, Academic Press, London, 1952.
Zollinger, H., Color Chemistry: Syntheses, Properties, and Applications of Organic Dyes and Pigments, 3$^{rd}$ Edit, VCH Wiley, 2003.

* cited by examiner

*Primary Examiner*—Eisa B Elhilo
(74) *Attorney, Agent, or Firm*—Finnegan, Henderson, Farabow, Garrett & Dunner, LLP

(57) ABSTRACT

The present disclosure relates to the use of cationic azo compounds with julolidine units as direct dyes, for the dyeing of keratin fibers, including human keratin fibers, such as the hair. The present disclosure also relates to a dyeing composition for the dyeing of keratin fibers, including human keratin fibers such as the hair, containing at least one cationic direct azo dye with julolidine units, in a suitable dyeing medium. The present disclosure also relates to a method of dyeing of keratin fibers, including human keratin fibers such as the hair, employing the dyeing composition according to the disclosure. The present disclosure also relates to cationic azo compounds with julolidine units.

35 Claims, No Drawings

CATIONIC AZO DYES WITH JULOLIDINE UNITS, DYEING COMPOSITION CONTAINING THEM, METHOD OF DYEING

CROSS-REFERENCE TO RELATED APPLICATIONS

This application claims benefit of priority under 35 U.S.C. § 119 to French Patent Application No. FR 05 08695, filed Aug. 23, 2005, the contents of which are incorporated herein by reference.

FIELD OF THE INVENTION

The present application relates to the use for the dyeing of keratin fibers, including human keratin fibers, such as the hair, of cationic azo compounds with julolidine units as direct dyes, a dyeing composition containing these azo compounds, a method of dyeing of fibers employing them, a kit with compartments and novel cationic azo compounds with julolidine units.

BACKGROUND OF THE INVENTION

The dyeing of keratin fibers, including human hair, with dyeing compositions containing oxidation dye precursors, generally called oxidation bases, such as ortho- or para-phenylenediamines, ortho- or para-aminophenols and heterocyclic compounds, is known. These oxidation bases are colorless or weakly colored compounds which, when combined with oxidizing products, can give rise by a process of oxidative condensation to colored compounds.

It is also known that it is possible to vary the shades obtained with these oxidation bases by combining them with dyeing coupling agents or modifiers, the latter being selected, for example, from aromatic meta-diamines, meta-aminophenols, meta-diphenols and certain heterocyclic compounds, such as indole compounds.

The wide range of molecules employed for the oxidation bases and the coupling agents gives a rich palette of colors.

The so-called "permanent" dyeing obtained using these oxidation dyes should, moreover, meet at least one of a certain number of requirements. Thus, it should ideally not cause any problems in toxicological terms, make it possible to obtain shades of the desired intensity, display good resistance to external agents, such as light, weather, washing, permanent waving, sweating and rubbing, provide coverage of white hair, and/or have minimum selectivity, i.e., give the smallest possible differences in coloration all the way along one and the same keratin fiber, which is generally sensitized (i.e. damaged) to a different degree between its tip and its root.

The dyeing of keratin fibers by direct or semi-permanent dyeing is also known. The method traditionally used in direct dyeing comprises applying direct dyes, which are colored and coloring molecules with affinity for the fibers, to the keratin fibers, waiting for a time to allow the colored molecules to penetrate, by diffusion, to the interior of the hairs, and then rinsing the fibers.

In contrast to the compositions for oxidation dyeing, the direct or semi-permanent dyeing compositions are used without the obligatory presence of an oxidizing agent. This dyeing can be carried out repeatedly without degrading the keratin fiber.

For example, the use of nitro benzene, anthraquinone, nitropyridine, azo, xanthene, acridine, azine or triarylmethane direct dyes is known.

The resulting coloration is often chromatic, but is, however, temporary or semi-permanent owing to the nature of the bonds between the direct dyes and the keratin fibers. These interactions mean that the dyes are readily desorbed from the surface and/or the core of the fiber. The coloration generally has poor resistance to washing or to sweating.

There is thus a real need for dyes with better performance, giving improvements in terms of uniformity of coloring, in relation to the quality of the hair that is dyed, shampoo and after-shampoo resistance (tenacity), restriction of scouring which leads to risks of patchiness, and/or color change over time when chromatic dyes are combined which have different respective tenacity.

Furthermore, the use of known cationic direct dyes makes it possible to obtain rich chromatic shades, which are, however, restricted to one color range (yellow, orange, red). Thus, there is a need for dyes outside of the known color range.

DETAILED DESCRIPTION OF THE INVENTION

The present inventors have now discovered that a class of cationic direct azo dyes with a so-called "julolidine" unit can provide at least one of these improvements.

Cationic dyes with the so-called "julolidine" unit are described in U.S. Pat. No. 4,341,853 for use as photosensitizers in electrophotography.

These azo compounds give dyes that may be resistant to external factors (e.g., sun and weather) as well as to shampooing and sweating. These compositions may have a good toxicological profile. In addition, these dyes may produce strong highlights, notably in the blue and violet shades. Whether alone or in combination with other traditional direct dyes or oxidation dyes, they make it possible to extend the color range.

A first aspect of the present disclosure thus relates to the use of cationic azo compounds with a julolidine unit as direct dyes for keratin fibers, including human keratin fibers, such as the hair.

A second aspect of the present disclosure comprises a dyeing composition for the dyeing of keratin fibers, including human keratin fibers, such as the hair, containing at least one cationic azo compound with a julolidine unit according to the present disclosure, in a medium suitable for dyeing.

The present disclosure also relates to a method of dyeing of keratin fibers, including human keratin fibers, such as the hair, employing the dyeing composition according to the present disclosure.

Another aspect of the present disclosure relates to the use of the composition for the dyeing of keratin fibers, including human keratin fibers, such as the hair.

The present disclosure further relates to a kit with compartments containing the dyeing composition according to the present disclosure.

Finally, another aspect of the present disclosure relates to cationic azo compounds with a julolidine unit.

Other characteristics, aspects, objects and advantages of the disclosure will become clearer on reading the description and the examples which follow.

It should be noted that in what follows, and unless stated otherwise, the limits of a range of values are included in that range.

The cationic azo compounds with a julolidine unit according to the present disclosure correspond to the compound of the following formula (I):

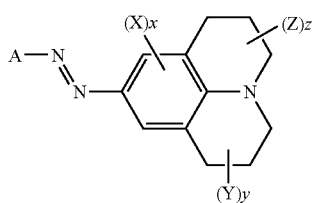

wherein:

A is chosen from cationic aromatic heterocycle compounds of the following formulae:

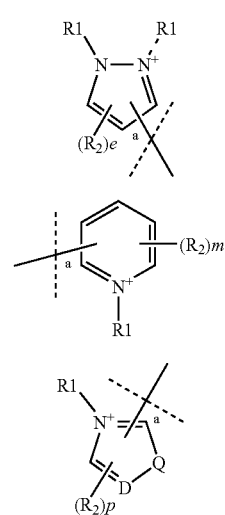

$R_1$ is chosen from, independently of one another:

linear and branched, saturated and unsaturated $C_1$-$C_{16}$ hydrocarbon chains, which optionally form at least one carbon ring with 3 to 7 ring members, optionally condensed with the aromatic ring, optionally substituted, optionally interrupted by at least one group chosen from heteroatoms chosen from oxygen, nitrogen and sulphur, and carbonyl groups; $R_1$ not containing a nitro, nitroso, peroxide and diazo bond; $R_1$ being directly attached to the nitrogen atom, quaternized or not, of the heteroaromatic ring A by a carbon atom.

$R_2$ is chosen from, independently of one another:

linear and branched, saturated and unsaturated $C_1$-$C_{16}$ hydrocarbon chains, which optionally form at least one aromatic or non-aromatic carbon ring, with 3 to 6 ring members, optionally substituted, optionally interrupted by at least one heteroatom or by at least one group bearing at least one heteroatom, such as heteroatoms chosen from oxygen and nitrogen;

hydroxyl groups, $C_1$-$C_4$ alkoxy groups, $C_2$-$C_4$ (poly)hydroxyalkoxy groups;

alkoxycarbonyl groups ($R_{11}O$—$CO$—) wherein $R_{11}$ is chosen from $C_1$-$C_4$ alkyl radicals;

alkylcarbonyloxy radicals ($R_{12}CO$—$O$—) wherein $R_{12}$ is chosen from $C_1$-$C_4$ alkyl radicals;

amino groups, amino groups substituted with one or two $C_1$-$C_4$ alkyl radicals, which may be identical or different, optionally bearing at least one hydroxyl group, where the two alkyl radicals can optionally form, with the nitrogen atom to which they are attached, a heterocycle with 5 or 6 ring members optionally bearing another heteroatom identical to or different from nitrogen, for example, oxygen or sulphur;

alkylcarbonylamino groups ($R_{13}CO$—$NR_{13}$—) and/or ($R_{13}CO$—$NH$) wherein the radicals $R_{13}$, independently of one another, are chosen from $C_1$-$C_4$ alkyl radicals;

carbamoyl groups (($R_{14})_2N$—$CO$) wherein the radicals $R_{14}$, independently of one another, which may be identical or different, are chosen from hydrogen atoms and $C_1$-$C_4$ alkyl radicals;

ureido groups (($R_{15})_2N$—$CO$—$NR_{16}$—) wherein the radicals $R_{15}$ and $R_{16}$, independently of one another, are chosen from hydrogen atoms and $C_1$-$C_4$ alkyl radicals;

sulphonamide groups (($R_{17})_2N$—$SO_2$—) wherein the radicals $R_{17}$, independently of one another, are chosen from hydrogen atoms and $C_1$-$C_4$ alkyl radicals;

alkylsulphonylamino groups ($R_{18}SO_2$—$NR_{19}$—) wherein the radicals $R_{18}$ and $R_{19}$, independently of one another, are chosen from hydrogen atoms and $C_1$-$C_4$ alkyl radicals;

guanidinium groups (($R_{20})_2N$—$C(=NH_2+)$—$NR_{21}$—) wherein the radicals $R_{20}$ and $R_{21}$, independently of one another, are chosen from hydrogen atoms and $C_1$-$C_4$ alkyl radicals;

nitro groups;

cyano groups;

halogen atoms, such as chlorine or fluorine;

two radicals $R_2$, carried by adjacent carbon atoms can form, together with the carbon atom to which each is attached, an aromatic or non-aromatic condensed ring;

m is an integer ranging from 0 to 4;

e is an integer ranging from 0 to 2;

p is an integer ranging from 0 to 1;

D is chosen from groups $CR_2$ and nitrogen atoms;

Q is chosen from groups $NR_1$, and atoms of oxygen or sulphur;

bond a arising from formulae (IIa), (IIb) or (IIc), joins group A to the azo group;

in the case of formulae (IIa), (IIb) or (IIc) and when two radicals $R_2$ carried by two adjacent carbon atoms form an aromatic ring, bond a can join group A to the azo group via the aromatic ring;

the electroneutrality of the compounds being provided by at least one anion $An^-$, which may be identical or different, cosmetically acceptable, including chloride, methylsulphate, methosulphate, tosylate, and acetate;

X, Y and Z are defined as possibilities of substitutions respectively on the alkyl and aryl rings of the three-ring nucleus;

x ranges from 0 to 2, y ranges from 0 to 6, and z ranges from 0 to 6, and x, y and z are integers;

or their addition salts or their solvates, with the exception of:

2-(9-julolidylazo)-3-methylbenzothiazolium perchlorate; and 2-(9-julolidylazo)-3-ethylthiazolium perchlorate, which are known sensitizers in electrophotography.

In the present disclosure, and unless stated otherwise:

When an alkyl radical or the alkyl part of a radical is said to be "substituted," it contains at least one substituent chosen from the groups:

hydroxyl, $C_1$-$C_4$ alkoxy and $C_2$-$C_4$ (poly)hydroxyalkoxy, amino, amino substituted with at least one $C_1$-$C_4$ alkyl group which may be identical or different, optionally bearing at least one hydroxyl group, said alkyl radicals, which can form, with the nitrogen atom to which they are attached, a heterocycle with 5 or 6 ring members, optionally containing at least one other heteroatom which may or may not be nitrogen.

When an aryl or heteroaryl radical or the aryl or heteroaryl part of a radical is said to be "substituted," such as by the substituent X on the aromatic ring of the three-ring nucleus, said (hetero) aryl radical or said (hetero) aryl part of a radical then comprises at least one substituent, which in the case of the aromatic ring of the julolidine unit is X, carried by a carbon atom and chosen from:

$C_1$-$C_{16}$, such as, for example, a $C_1$-$C_8$, alkyl radicals, optionally substituted with at least one radical chosen from the radicals hydroxy, $C_1$-$C_2$ alkoxy, $C_2$-$C_4$ (poly)-hydroxyalkoxy, acylamino, amino substituted with one or two $C_1$-$C_4$ alkyl radicals, which may be identical or different, optionally bearing at least one hydroxyl group or the two radicals which can form, with the nitrogen atom to which they are attached, a heterocycle with 5 or 7 ring members, such as, for example, 5 or 6 ring members, optionally containing another heteroatom identical to or different from nitrogen;

halogen atoms such as chlorine, fluorine or bromine;

hydroxyl groups;

$C_1$-$C_2$ alkoxy radicals;

$C_2$-$C_4$ (poly)-hydroxyalkoxy radicals;

amino radicals;

amino radicals substituted with one or two $C_1$-$C_4$ alkyl radicals, which may be identical or different, optionally bearing at least one hydroxyl group;

acylamino radicals (—$NR_{31}$—$COR_{32}$) wherein the radical $R_{31}$ is chosen from hydrogen atoms and $C_1$-$C_4$ alkyl radicals optionally bearing at least one hydroxyl group and the radical $R_{32}$ is chosen from $C_1$-$C_2$ alkyl radicals;

carbamoyl radicals (($R_{33}$)$_2$N—CO—) wherein the radicals $R_{33}$, which may be identical or different, are chosen from hydrogen atoms and $C_1$-$C_4$ alkyl radicals optionally bearing at least one hydroxyl group;

alkylsulphonylamino radicals ($R_{34}SO_2$—$NR_{35}$—) wherein the radical $R_{34}$ is chosen from hydrogen atoms and $C_1$-$C_4$ alkyl radicals optionally bearing at least one hydroxyl group and the radical $R_{35}$ is chosen from $C_1$-$C_4$ alkyl radicals and phenyl radicals;

aminosulphonyl radicals (($R_{36}$)$_2$N—$SO_2$—) wherein the radicals $R_{36}$, which may be identical or different, are chosen from hydrogen atoms and $C_1$-$C_4$ alkyl radicals optionally bearing at least one hydroxyl group.

When the cyclic or heterocyclic part of a non-aromatic radical is said to be "substituted," such as by the substituents Y and Z of the aliphatic heterocycles of the three-ring nucleus, it then comprises at least one substituent, which in the case of the nonaromatic rings of the julolidine unit is Y and Z, carried by a carbon atom chosen from the groups:

hydroxyl, $C_1$-$C_4$ alkoxy and $C_2$-$C_4$ (poly)hydroxyalkoxy, alkylcarbonylamino (($R_{41}$CO—$NR_{42}$—) wherein the radical $R_{42}$ is chosen from hydrogen atoms and $C_1$-$C_4$ alkyl radicals optionally bearing at least one hydroxyl group and the radical $R_{41}$ is chosen from $C_1$-$C_2$ alkyl radicals and amino radicals substituted with two $C_1$-$C_4$ alkyl groups which may be identical or different optionally bearing at least one hydroxyl group, said alkyl radicals can form, with the nitrogen atom to which they are attached, a heterocycle with 5 or 6 ring members, optionally containing at least one other heteroatom which may or may not be nitrogen.

When a ring does not carry the maximum number of substituents, the unsubstituted position or positions then carry a hydrogen atom.

In at least one embodiment, $R_1$ is chosen from $C_1$-$C_8$ alkyls and hydroxyalkyl groups.

According to at least one embodiment of the present disclosure, formulae (IIa), (IIb) and (IIc) are such that they contain two radicals $R_2$ carried by adjacent carbon atoms, said radicals then forming, together with the carbon atom to which each is attached, an aromatic condensed ring, optionally substituted.

According to at least one embodiment of the present disclosure, e, m and p have a value of 0.

In at least one embodiment, x has a value of 0 or 1 with X chosen from alkyl, hydroxyl, hydroxyalkyl, alkoxy, amino, alkylamino, dialkylamino, and acylamino groups; wherein the term "alkyl" denotes a $C_1$-$C_6$ chain, optionally substituted, and "acyl" denoting alkylcarbonyl.

The following compounds may be mentioned as examples of compounds of formula (I) that can be used according to at least one embodiment of the present disclosure:

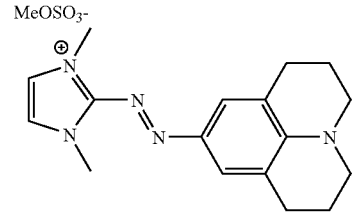

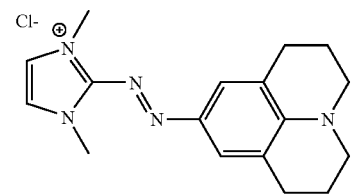

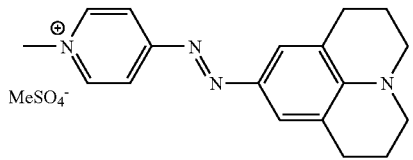

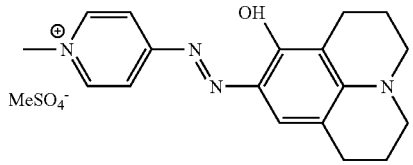

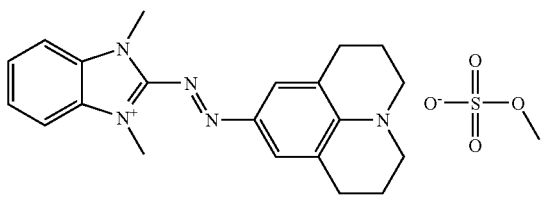

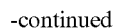

The dyes corresponding to the formula can be obtained, for example, by four different routes of synthesis, hereinafter called respectively route A, route B, route C and route D:

In the following schemes, the definition of B, non-cationic precursor of A, corresponds to the following 3 formulae:

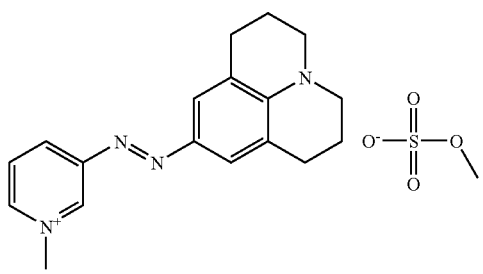

Hereinafter, HAL denotes a halogen group joined to $R_1$ by one of its carbon atoms, for example, a chloro, bromo or iodo group, or alternatively an alkylsulphato group, such as methylsulphato or ethylsulphato or alternatively methylsulphonato (mesylate) or arylsulphonato (tosylate).

1/Route of Synthesis A

The compound of formula (I) is obtained in three successive stages according to the following scheme:

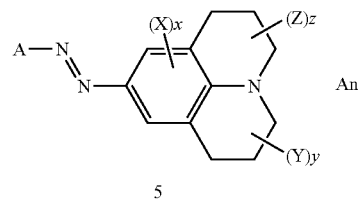

The diazonium salt 2 of the heteroaromatic amine $BNH_2$ 1 is prepared by classical methods (H Zollinger, Color Chemistry, Wiley VCH Ed 2003 and The Chemistry of synthetic dyes, Academic Press, London, vol II, 1952). Then the diazonium salt 2 is reacted with a compound 3 (an aromatic amine with a julolidine unit) to form compound 4. This type of coupling is well known in the literature cited above.

The third stage comprises reacting compound 4 with an alkylating agent, such as an alkyl sulphate, an alkyl halide, an alkyl alkylsulphonate or an alkyl arylsulphonate, to form compound 5: a cationic direct azo dye with a julolidine unit.

The alkylation reaction is carried out for example in a halogenated solvent (dichloromethane) or ester (ethyl acetate), at a temperature below 150° C., with, for example, solvent reflux. These conditions are notably described in the literature. As reference to this type of reaction, Advanced Organic Synthesis 5th Ed M. Smith and J. March John Wiley & Sons Ed, 2001 and International Application No. WO 03/060015 may be mentioned, for example.

2/Route of Synthesis B

The compound of formula (I) can be obtained by diazotation of the para-aminated derivative of an aromatic amine with a julolidine unit 6, then coupling of the diazonium salt 7 obtained with a heterocycle to give compound 8, then alkylation of the heterocyclic function to give compound 9 (the cationic direct azo dye with a julolidine unit) according to the following scheme:

-continued

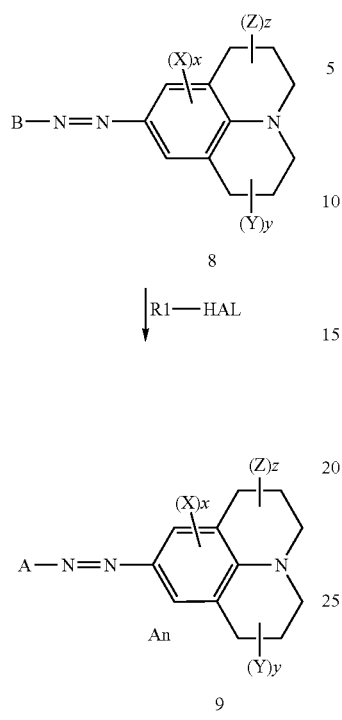

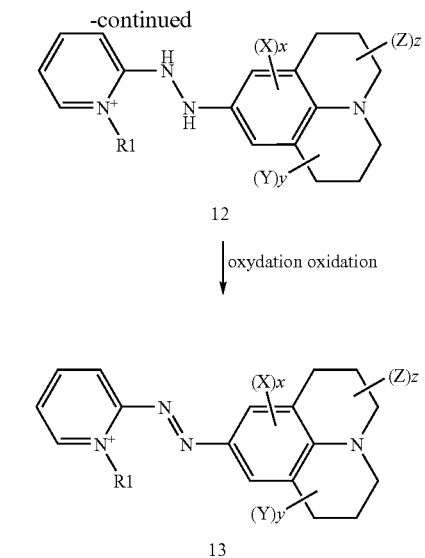

The reaction for forming compound 12 can be carried out in a polar solvent, such as an alcohol or DMF, at a temperature below 150° C., in the presence if necessary of a base less nucleophilic than the hydrazine selected (J. Med. Chem. 1996, 39 (2), 570-581). Oxidation can be carried out with the usual oxidizing agents: N-bromosuccinimide, ferric chloride, manganese oxide, chromium oxides, hydrogen peroxide, and peracids, and, in at least one embodiment, in an acid environment and at a temperature below 100° C. for less than twenty-four hours.

4/Route of Synthesis D

The compound of formula (I) can also be obtained by oxidative coupling. This route is described in the literature. For reference to this type of reaction, mention may be made, for example, of Angew. Chem. 1958, 70,215; Angew. Chem., Int. Ed., 1962, 1,640 and H Zollinger, Color Chemistry 3rd Ed, VCH Wiley, 2003. The route is exemplified by the following scheme, using pyridinium to illustrate the heterocycle, such as compound 14 to give compound 17 (a cationic direct azo dye with a julolidine unit):

All the stages of synthesis are described in the literature and the references for route 1 are also applicable.

The second stage comprises reacting the diazonium salt 7 obtained beforehand with a heterocycle B-H (following the previous definition of B and H representing a hydrogen atom bound to B on the position which will then be that of the azo group).

3/Route of Synthesis C

The compound of formula (I) can also be obtained in two stages of synthesis: nucleophilic attack on a carbon atom of a cationic heterocycle [11] by a para-hydrazino compound of an aromatic amine with a julolidine unit 10 then oxidation of the compound 12 obtained to give compound 13 (a cationic direct azo dye with a julolidine unit). These reactions are exemplified below with a cationic heterocycle of the pyridinium type and with compound 11 according to the following scheme:

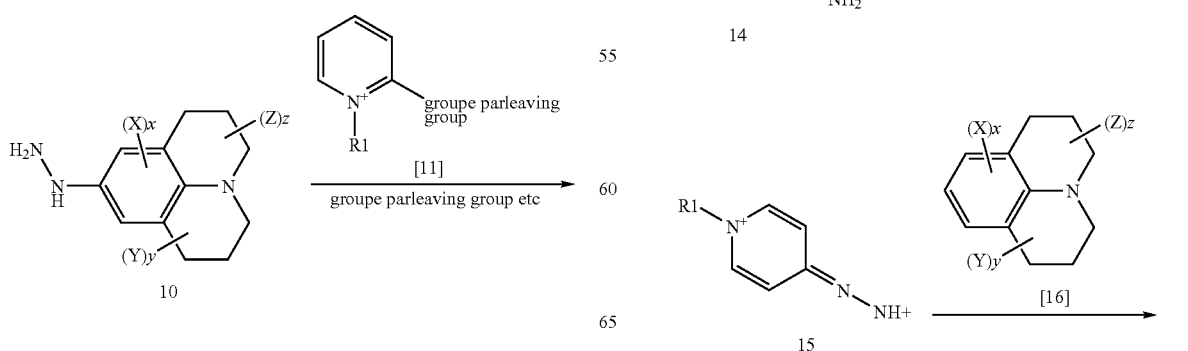

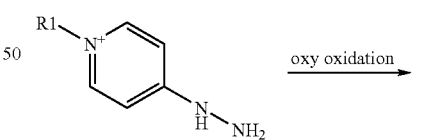

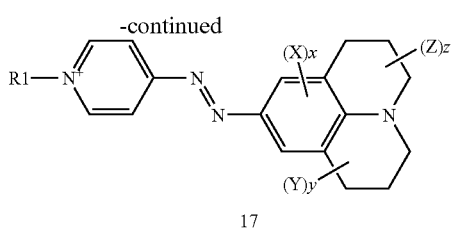

The starting reactants are commercially available or are obtained by methods known by a person skilled in the art, advantageously starting from commercially available compounds.

The present disclosure also relates to the use of cationic azo compounds with a julolidine unit corresponding to the compound of the following formula (I):

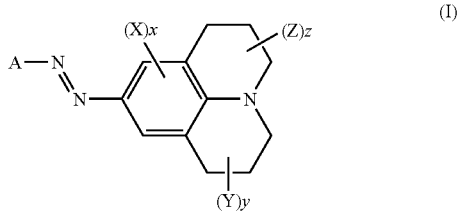

wherein:

A is a cationic aromatic heterocycle compound chosen from compounds of the following formulae:

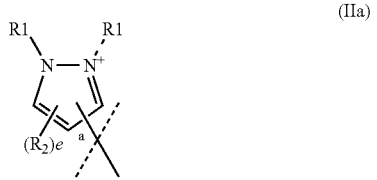

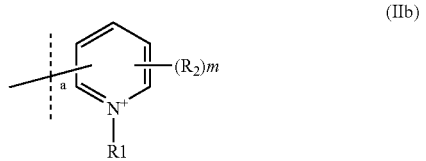

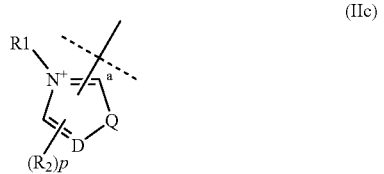

$R_1$ is chosen from, independently of one another:

linear and branched, saturated and unsaturated $C_1$-$C_{16}$ hydrocarbon chain, which can optionally form at least one carbon ring with 3 to 7 ring members, optionally condensed with the aromatic ring, optionally substituted, optionally interrupted by at least one group chosen from heteroatoms such as oxygen, nitrogen or sulphur, and the carbonyl group; $R_1$ not containing a nitro, nitroso, peroxide and diazo bond; $R_1$ being directly attached to the nitrogen atom, quaternized or not, of the heteroaromatic ring A by a carbon atom.

$R_2$ is chosen from, independently of one another:

linear and branched, saturated and unsaturated $C_1$-$C_{16}$ hydrocarbon chain, which can form at least one aromatic or non-aromatic carbon ring, with 3 to 6 ring members, optionally substituted, optionally interrupted by at least one heteroatom or by at least one group bearing at least one heteroatom, such as oxygen or nitrogen;

hydroxyl groups, $C_1$-$C_4$ alkoxy groups, $C_2$-$C_4$ (poly)hydroxyalkoxy groups;

alkoxycarbonyl groups ($R_{11}$O—CO—) wherein $R_{11}$ is chosen from $C_1$-$C_4$ alkyl radicals;

alkylcarbonyloxy radicals ($R_{12}$CO—O—) wherein $R_{12}$ is chosen from $C_1$-$C_4$ alkyl radicals;

amino groups and amino groups substituted with one or two $C_1$-$C_4$ alkyl radicals, which may be identical or different, optionally bearing at least one hydroxyl group, where the two alkyl radicals can optionally form, with the nitrogen atom to which they are attached, a heterocycle with 5 or 6 ring members optionally bearing another heteroatom identical to or different from nitrogen, for example oxygen or sulphur;

alkylcarbonylamino groups ($R_{13}$CO—$NR_{13}$—) and/or ($R_{13}$CO—NH) wherein the radicals $R_{13}$, independently of one another, are chosen from $C_1$-$C_4$ alkyl radicals;

carbamoyl groups (($R_{14}$)$_2$N—CO) wherein the radicals $R_{14}$, independently of one another, which may be identical or different, are chosen from hydrogen atoms and $C_1$-$C_4$ alkyl radicals;

ureido groups (($R_{15}$)$_2$N—CO—$NR_{16}$—) wherein the radicals $R_{15}$ and $R_{16}$, independently of one another, are chosen from hydrogen atoms and $C_1$-$C_4$ alkyl radicals;

sulphonamide groups (($R_{17}$)$_2$N—SO$_2$—) wherein the radicals $R_{17}$, independently of one another, are chosen from hydrogen atoms and $C_1$-$C_4$ alkyl radicals;

alkylsulphonylamino groups ($R_{18}$SO$_2$—$NR_{19}$—) wherein the radicals $R_{18}$ and $R_{19}$, independently of one another, are chosen from hydrogen atoms and $C_1$-$C_4$ alkyl radicals;

guanidinium groups (($R_{20}$)$_2$N—C(=$NH_2$+)—$NR_{21}$-) wherein the radicals $R_{20}$ and $R_{21}$, independently of one another, are chosen from hydrogen atoms and $C_1$-$C_4$ alkyl radicals;

nitro groups;

cyano groups;

halogen atoms, such as chlorine or fluorine;

two radicals $R_2$, carried by adjacent carbon atoms, can form, together with the carbon atom to which each is attached, an aromatic or non-aromatic condensed ring;

m is an integer ranging from 0 to 4;

e is an integer ranging from 0 to 2;

p is an integer ranging from 0 to 1;

D is chosen from groups $CR_2$ and nitrogen atoms;

Q is chosen from groups $NR_1$ and atoms of oxygen or sulphur;

the bond a from formulae (IIa), (IIb) or (IIc), joins group A to the azo group;

in the case of formulae (IIa), (IIb) or (IIc) and when two radicals $R_2$ carried by two adjacent carbon atoms form an aromatic ring, bond a can join group A to the azo group via the aromatic ring;

the electroneutrality of the compounds being provided by at least one anion An⁻, which may be identical or different, cosmetically acceptable, including chloride, methylsulphate, methosulphate, tosylate, and acetate;

X, Y and Z are defined as possibilities of substitutions respectively on the alkyl and aryl rings of the three-ring nucleus;

x ranges from 0 to 2, y ranges from 0 to 6, and z ranges from 0 to 6, wherein x, y and z are integers;

or their addition salts or their solvates.

In what follows, and unless stated otherwise:

When an alkyl radical or the alkyl part of a radical is said to be "substituted," it contains at least one substituent chosen from the groups:

hydroxyl, $C_1$-$C_4$ alkoxy and $C_2$-$C_4$ (poly)hydroxyalkoxy, amino and amino substituted with at least one $C_1$-$C_4$ alkyl group, which may be identical or different optionally bearing at least one hydroxyl group, and the alkyl radicals optionally form, with the nitrogen atom to which they are attached, a heterocycle with 5 or 6 ring members, optionally containing at least one other heteroatom which may or may not be nitrogen.

When an aryl or heteroaryl radical or the aryl or heteroaryl part of a radical is said to be "substituted," said substituted aryl or heteroaryl comprises at least one substituent carried by a carbon atom, wherein for the aromatic ring of the three ring nucleus of said julolidine unit said substituent is X, and wherein X or said at least one substituent is chosen from:

$C_1$-$C_6$, such as $C_1$-$C_8$, alkyl radicals, optionally substituted with at least one radical chosen from the radicals hydroxy, $C_1$-$C_2$ alkoxy, $C_2$-$C_4$ (poly)-hydroxyalkoxy, acylamino, amino substituted with one or two $C_1$-$C_4$ alkyl radicals, which may be identical or different, optionally bearing at least one hydroxyl group or where the two radicals can form, with the nitrogen atom to which they are attached, a heterocycle with 5 or 7 ring members, such as 5 or 6 ring members, optionally containing another heteroatom identical to or different from nitrogen;

halogen atoms such as chlorine, fluorine or bromine;

hydroxyl groups;

$C_1$-$C_2$ alkoxy radicals; $C_2$-$C_4$ (poly)-hydroxyalkoxy radicals;

amino radicals;

amino radicals substituted with one or two $C_1$-$C_4$ alkyl radicals, which may be identical or different, optionally bearing at least one hydroxyl group;

acylamino radicals (—$NR_{31}$—$COR_{32}$) wherein the radical $R_{31}$ is chosen from hydrogen atoms and $C_1$-$C_4$ alkyl radicals optionally bearing at least one hydroxyl group and the radical $R_{32}$ is chosen from $C_1$-$C_2$ alkyl radicals;

carbamoyl radicals (($R_{33}$)$_2$N—CO—) wherein the radicals $R_{33}$, which may be identical or different, are chosen from hydrogen atoms and $C_1$-$C_4$ alkyl radicals optionally bearing at least one hydroxyl group;

alkylsulphonylamino radicals ($R_{34}$$SO_2$—$NR_{35}$—) wherein the radical $R_{34}$ is chosen from hydrogen atoms and $C_1$-$C_4$ alkyl radicals optionally bearing at least one hydroxyl group and the radical $R_{35}$ is chosen from $C_1$-$C_4$ alkyl radicals and phenyl radicals;

aminosulphonyl radicals (($R_{36}$)$_2$N—$SO_2$—) wherein the radicals $R_{36}$, which may be identical or different, are chosen from hydrogen atoms and $C_1$-$C_4$ alkyl radicals optionally bearing at least one hydroxyl group.

When the cyclic or heterocyclic part of a non-aromatic radical is said to be "substituted," it comprises at least one substituent carried by a carbon atom, wherein for the non-aromatic rings of the three ring nucleus of said julolidine unit said substituents are Y and Z, and wherein Y and Z or said at least one substituent is chosen from:

hydroxyl, $C_1$-$C_4$ alkoxy and $C_2$-$C_4$ (poly)hydroxyalkoxy, and alkylcarbonylamino (($R_{41}$CO—$NR_{42}$—) wherein the radical $R_{42}$ is chosen from hydrogen atoms and $C_1$-$C_4$ alkyl radicals optionally bearing at least one hydroxyl group and the radical $R_{41}$ is chosen from $C_1$-$C_2$ alkyl radicals and amino radicals substituted with two $C_1$-$C_4$ alkyl groups which may be identical or different optionally bearing at least one hydroxyl group, said alkyl radicals which can form, with the nitrogen atom to which they are attached, a heterocycle with 5 or 6 ring members, optionally containing at least one other heteroatom which may or may not be nitrogen.

When a ring does not carry the maximum number of substituents, the unsubstituted position or positions then carry a hydrogen atom.

In at least one embodiment, $R_1$ is chosen from $C_1$-$C_8$ alkyl and hydroxyalkyl groups.

According to at least one embodiment of the present disclosure, formulae (IIa), (IIb) and (IIc) are such that they contain two radicals $R_2$ carried by adjacent carbon atoms, said radicals then forming, together with the carbon atom to which each is attached, an aromatic condensed ring, optionally substituted.

According to at least one embodiment, e, m and p have the value 0.

In at least one embodiment of the present disclosure, x has a value of 0 or 1 with X being chosen from alkyl, hydroxyl, hydroxyalkyl, alkoxy, amino, alkylamino, dialkylamino, and acylamino groups; wherein alkyl denotes a $C_1$-$C_6$ chain optionally substituted, and acyl denotes alkylcarbonyl.

The following compounds may be mentioned as non-limiting examples of compounds of formula (I) that can be used according to the present disclosure:

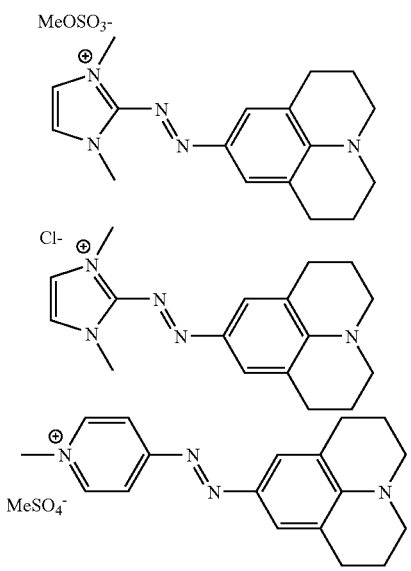

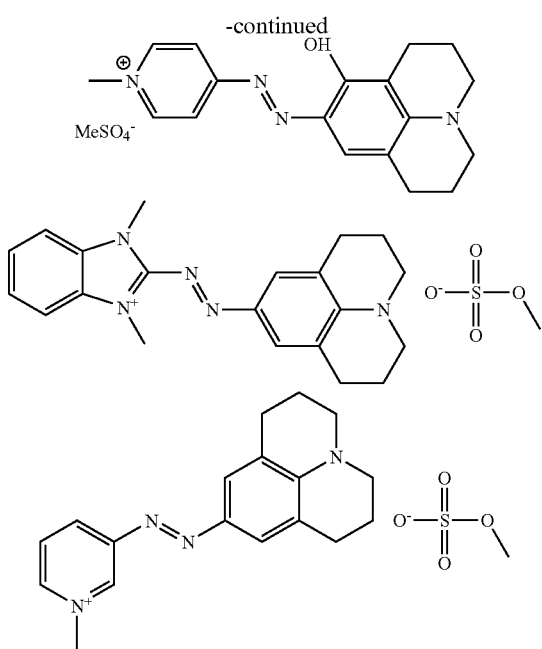

The present disclosure also relates to a dyeing composition for the dyeing of keratin fibers, including human keratin fibers, such as the hair, containing, in a suitable dyeing medium, at least one cationic azo compound as defined above for use as a direct dye.

The dyeing composition according to at least one embodiment of the present disclosure can contain from 0.001 to 20 wt. %, such as from 0.01 to 10 wt. %, of cationic direct azo dye of formula (I) relative to the total weight of the composition.

In at least one embodiment, the composition of the present disclosure may also include at least one oxidation base.

For example, the oxidation bases may be chosen from phenylenediamines, bis-phenylalkylenediamines, para-aminophenols, ortho-aminophenols, heterocyclic bases and their addition salts.

Among the paraphenylenediamines that may be used according to at least one embodiment of the present disclosure, the following may be mentioned as non-limiting examples: paraphenylenediamine, paratoluylenediamine, 2-chloro paraphenylenediamine, 2,3-dimethyl paraphenylenediamine, 2,6-dimethyl paraphenylenediamine, 2,6-diethyl paraphenylenediamine, 2,5-dimethyl paraphenylenediamine, N,N-dimethyl paraphenylenediamine, N,N-diethyl paraphenylenediamine, N,N-dipropyl paraphenylenediamine, 4-amino N,N-diethyl 3-methyl aniline, N,N-bis-(β-hydroxyethyl) paraphenylenediamine, 4-N,N-bis-(β-hydroxyethyl)amino-2-methylaniline, 4-N,N-bis-(β-hydroxyethyl)amino-2-chloro aniline, 2-β-hydroxyethyl paraphenylenediamine, 2-fluoro paraphenylenediamine, 2-isopropyl paraphenylenediamine, N-(β-hydroxypropyl) paraphenylenediamine, 2-hydroxymethyl paraphenylenediamine, N,N-dimethyl 3-methyl paraphenylenediamine, N,N-(ethyl, β-hydroxyethyl) paraphenylenediamine, N-(β,γ-dihydroxypropyl) paraphenylenediamine, N-(4'-aminophenyl) paraphenylenediamine, N-phenyl paraphenylenediamine, 2-β-hydroxyethyloxy paraphenylenediamine, 2-β-acetylaminoethyloxy paraphenylenediamine, N-(β-methoxyethyl) paraphenylenediamine, 4-aminophenylpyrrolidine, 2-thienyl paraphenylenediamine, 2-βhydroxyethylamino 5-amino toluene, 3-hydroxy 1-(4'-aminophenyl)pyrrolidine and their acid-addition salts.

Among the paraphenylenediamines mentioned above, paraphenylenediamine, paratoluylenediamine, 2-isopropyl paraphenylenediamine, 2-β-hydroxyethyl paraphenylenediamine, 2-β-hydroxyethyloxy paraphenylenediamine, 2,6-dimethyl paraphenylenediamine, 2,6-diethyl paraphenylenediamine, 2,3-dimethyl paraphenylenediamine, N,N-bis-(β-hydroxyethyl) paraphenylenediamine, 2-chloro paraphenylenediamine, 2-β-acetylaminoethyloxy paraphenylenediamine, and their acid-addition salts are used according to at least one embodiment.

Among the bis-phenylalkylenediamines, the following may be mentioned as non-limiting examples: N,N'-bis-(β-hydroxyethyl) N,N'-bis-(4'-aminophenyl) 1,3-diamino propanol, N,N'-bis-(β-hydroxyethyl) N,N'-bis-(4'-aminophenyl) ethylenediamine, N,N'-bis-(4-aminophenyl) tetramethylenediamine, N,N'-bis-(β-hydroxyethyl) N,N'-bis-(4-aminophenyl) tetramethylenediamine, N,N'-bis-(4-methyl-aminophenyl) tetramethylenediamine, N,N'-bis-(ethyl) N,N'-bis-(4'-amino, 3'-methylphenyl) ethylenediamine, 1,8-bis-(2,5-diamino phenoxy)-3,6-dioxaoctane, and their addition salts.

Among the para-aminophenols, the following may be mentioned as non-limiting examples: para-aminophenol, 4-amino 3-methyl phenol, 4-amino 3-fluoro phenol, 4-amino-3-chlorophenol, 4-amino 3-hydroxymethyl phenol, 4-amino 2-methyl phenol, 4-amino 2-hydroxymethyl phenol, 4-amino 2-methoxymethyl phenol, 4-amino 2-aminomethyl phenol, 4-amino 2-(β-hydroxyethyl aminomethyl) phenol, 4-amino 2-fluoro phenol, and their acid-addition salts.

Among the ortho-aminophenols, the following may be mentioned as non-limiting examples: 2-amino phenol, 2-amino 5-methyl phenol, 2-amino 6-methyl phenol, 5-acetamido 2-amino phenol, and their addition salts.

Among the heterocyclic bases, the following may be mentioned as non-limiting examples: pyridine derivatives, pyrimidine derivatives and pyrazole derivatives.

Among the pyridine derivatives, non-limiting mention may be made of the compounds described for example in British Patent Nos. GB 1,026,978 and GB 1,153,196, as well as 2,5-diamino pyridine, 2-(4-methoxyphenyl)amino 3-amino pyridine, 3,4-diamino pyridine, and their addition salts.

Among other pyridine oxidation bases that can be used in the present disclosure, non-limiting mention may be made of the 3-amino pyrazolo-[1,5-a]-pyridine oxidation bases or their addition salts described for example in French Patent Application No. FR 2 801 308. As examples, non-limiting mention may be made of pyrazolo[1,5-a]pyridin-3-ylamine; 2-acetylamino pyrazolo-[1,5-a]pyridin-3-ylamine; 2-morpholin-4-yl-pyrazolo[1,5-a]pyridin-3-ylamine; 3-aminopyrazolo[1,5-a]pyridine-2-carboxylic acid; 2-methoxy-pyrazolo[1,5-a]pyridin-3-ylamino; (3-amino-pyrazolo[1,5-a]pyridin-7-yl)-methanol; 2-(3-amino-pyrazolo[1,5-a]pyridin-5-yl)-ethanol; 2-(3-amino-pyrazolo[1,5-a]pyridin-7-yl)-ethanol; (3-amino-pyrazolo[1,5-a]pyridin-2-yl)-methanol; 3,6-diamino-pyrazolo[1,5-a]pyridine; 3,4-diamino-pyrazolo[1,5-a]pyridine; pyrazolo[1,5-a]pyridine-3,7-diamine; 7-morpholin-4-yl-pyrazolo[1,5-a]pyridin-3-ylamine; pyrazolo[1,5-a]pyridine-3,5-diamine; 5-morpholin-4-yl-pyrazolo[1,5-a]pyridin-3-ylamine; 2-[(3-amino-pyrazolo[1,5-a]pyridin-5-yl)-(2-hydroxyethyl)-amino]-ethanol; 2-[(3-amino-pyrazolo[1,5-a]pyridin-7-yl)-(2-hydroxyethyl)-amino]-ethanol; 3-amino-pyrazolo[1,5-a]pyridin-5-ol; 3-amino-pyrazolo[1,5-a]pyridin-4-ol; 3-amino-pyrazolo[1,5-a]pyridin-6-ol; 3-amino-pyrazolo[1,5-a]pyridin-7-ol; as well as their addition salts.

Among the pyrimidine derivatives, non-limiting mention may be made of the compounds described for example in German Patent No. DE 23 59 399; Japanese Patent Nos. JP 88-169571 and JP 05-63124; European Patent No. EP 0 770 375 and International Patent Application No. WO 96/15765, such as 2,4,5,6-tetra-aminopyrimidine, 4-hydroxy 2,5,6-tri-aminopyrimidine, 2-hydroxy 4,5,6-triaminopyrimidine, 2,4-dihydroxy 5,6-diaminopyrimidine, 2,5,6-triaminopyrimidine and their addition salts and their tautomeric forms, when a tautomeric equilibrium exists.

Among the pyrazole derivatives, non-limiting mention may be made of the compounds described in German Patent Nos. DE 38 43 892 and DE 41 33 957; International Patent Application Nos. WO 94/08969 and WO 94/08970; French Patent Application No. FR-A-2 733 749; and German Patent Application No. DE 195 43 988, such as 4,5-diamino 1-methyl pyrazole, 4,5-diamino 1-(β-hydroxyethyl) pyrazole, 3,4-diamino pyrazole, 4,5-diamino 1-(4'-chlorobenzyl) pyrazole, 4,5-diamino 1,3-dimethyl pyrazole, 4,5-diamino 3-methyl 1-phenyl pyrazole, 4,5-diamino 1-methyl 3-phenyl pyrazole, 4-amino 1,3-dimethyl 5-hydrazino pyrazole, 1-benzyl 4,5-diamino 3-methyl pyrazole, 4,5-diamino 3-tert-butyl 1-methyl pyrazole, 4,5-diamino 1-tert-butyl 3-methyl pyrazole, 4,5-diamino 1-(β-hydroxyethyl) 3-methyl pyrazole, 4,5-diamino 1-ethyl 3-methyl pyrazole, 4,5-diamino 1-ethyl 3-(4'-methoxyphenyl) pyrazole, 4,5-diamino 1-ethyl 3-hydroxymethyl pyrazole, 4,5-diamino 3-hydroxymethyl 1-methyl pyrazole, 4,5-diamino 3-hydroxymethyl 1-isopropyl pyrazole, 4,5-diamino 3-methyl 1-isopropyl pyrazole, 4-amino 5-(2'-aminoethyl)amino 1,3-dimethyl pyrazole, 3,4,5-triamino pyrazole, 1-methyl 3,4,5-triamino pyrazole, 3,5-diamino 1-methyl 4-methylamino pyrazole, 3,5-diamino 4-(β-hydroxyethyl)amino 1-methyl pyrazole, and their addition salts. It is also possible to use 4,5-diamino 1-(β-methoxyethyl)pyrazole.

In at least one embodiment, the oxidation base or bases present in the composition of the present disclosure are present in an amount ranging from 0.001 to 20 wt. % of the total weight of the dyeing composition, such as, for example, from 0.005 to 6 wt. %.

If the composition contains at least one oxidation base, the composition according to at least one embodiment of the disclosure may contain at least one coupling agent used conventionally for the dyeing of keratin fibers. Among these coupling agents, non-limiting mention may be made of the meta-phenylenediamines, meta-aminophenols, meta-diphenols, naphthalenic coupling agents, and heterocyclic coupling agents, as well as their addition salts.

As non-limiting examples, mention may be made of 1,3-dihydroxy benzene, 1,3-dihydroxy 2-methyl benzene, 4-chloro 1,3-dihydroxy benzene, 2,4-diamino 1-(β-hydroxyethyloxy) benzene, 2-amino 4-(β-hydroxyethylamino) 1-methoxybenzene, 1,3-diamino benzene, 1,3-bis-(2,4-diaminophenoxy) propane, 3-ureido aniline, 3-ureido 1-dimethylamino benzene, sesamol, 1-β-hydroxyethylamino-3,4-methylenedioxybenzene, α-naphthol, 2 methyl-1-naphthol, 6-hydroxy indole, 4-hydroxy indole, 4-hydroxy N-methyl indole, 2-amino-3-hydroxy pyridine, 6-hydroxy benzomorpholine, 3,5-diamino-2,6-dimethoxypyridine, 1-N-(β-hydroxyethyl)amino-3,4-methylene dioxybenzene, 2,6-bis-(β-hydroxyethylamino)toluene and their addition salts.

In at least one embodiment of the composition of the present disclosure, the coupling agent or agents are present in an amount ranging from 0.001 to 20 wt. % of the total weight of the dyeing composition, such as, for example, from 0.005 to 6 wt. %.

In at least one embodiment, the addition salts of the oxidation bases and of the coupling agents that are used within the scope of the present disclosure are selected from the acid-addition salts such as hydrochlorides, hydrobromides, sulphates, citrates, succinates, tartrates, lactates, tosylates, benzenesulphonates, phosphates and acetates and base-addition salts such as soda, potash, ammonia, amines or alkanolamines.

The dyeing composition according to at least one embodiment of the present disclosure can contain at least one additional direct dye other than the cationic azo direct dyes of formula (I) according to the present disclosure, which can be chosen from the nitro dyes of the neutral, acid or cationic benzene series, the neutral, acid or cationic azo direct dyes, the quinone direct dyes and, for example, neutral, acid or cationic anthraquinone direct dyes, azine direct dyes, triarylmethane direct dyes, indoamino direct dyes and natural direct dyes. As non-limiting examples, mention may be made of benzene nitro dyes, the azo, azomethine, methine, tetraazapentamethine, anthraquinone, naphthoquinone, benzoquinone, phenothiazine indigoid, xanthene, phenanthridine, and phthalocyanine dyes, those derived from triarylmethane and the natural dyes, alone or in mixtures.

Among the benzene direct dyes that can be used according to the present disclosure, non-limiting mention may be made of the following compounds:

1,4-diamino-2-nitrobenzene,
1-amino-2 nitro-4-β-hydroxyethylaminobenzene,
1-amino-2 nitro-4-bis(β-hydroxyethyl)-aminobenzene,
1,4-bis(β-hydroxyethylamino)-2-nitrobenzene,
1-β-hydroxyethylamino-2-nitro-4-bis-(β-hydroxyethylamino)-benzene,
1-β-hydroxyethylamino-2-nitro-4-aminobenzene,
1-β-hydroxyethylamino-2-nitro-4-(ethyl)(β-hydroxyethyl)-aminobenzene,
1-amino-3-methyl-4-β-hydroxyethylamino-6-nitrobenzene,
1-amino-2-nitro-4-β-hydroxyethylamino-5-chlorobenzene,
1,2-diamino-4-nitrobenzene,
1-amino-2-β-hydroxyethylamino-5-nitrobenzene,
1,2-bis-(β-hydroxyethylamino)-4-nitrobenzene,
1-amino-2-tris-(hydroxymethyl)-methylamino-5-nitrobenzene,
1-hydroxy-2-amino-5-nitrobenzene,
1-hydroxy-2-amino-4-nitrobenzene,
1-hydroxy-3-nitro-4-aminobenzene,
1-hydroxy-2-amino-4,6-dinitrobenzene,
1-β-hydroxyethyloxy-2-β-hydroxyethylamino-5-nitrobenzene,
1-methoxy-2-β-hydroxyethylamino-5-nitrobenzene,
1-β-hydroxyethyloxy-3-methylamino-4-nitrobenzene,
1-β,γ-dihydroxypropyloxy-3-methylamino-4-nitrobenzene,
1-β-hydroxyethylamino-4-β,γ-dihydroxypropyloxy-2-nitrobenzene,
1-β,γ-dihydroxypropylamino-4-trifluoromethyl-2-nitrobenzene,
1-β-hydroxyethylamino-4-trifluoromethyl-2-nitrobenzene,
1-β-hydroxyethylamino-3-methyl-2-nitrobenzene,
1-β-aminoethylamino-5-methoxy-2-nitrobenzene,
1-hydroxy-2-chloro-6-ethylamino-4-nitrobenzene,
1-hydroxy-2-chloro-6-amino-4-nitrobenzene,
1-hydroxy-6-bis-(β-hydroxyethyl)-amino-3-nitrobenzene,
1-β-hydroxyethylamino-2-nitrobenzene, and 1-hydroxy-4-β-hydroxyethylamino-3-nitrobenzene.

Among the direct azo dyes that can be used according to the present disclosure, non-limiting mention may be made of the cationic azo dyes described in International Patent Application Nos. WO 95/15144 and WO-95/01772 and European Patent Application No. EP-714 954, the contents of which are incorporated by reference herein.

Among these compounds, non-limiting mention may be made of the following dyes:
- 1,3-dimethyl-2-[[4-(dimethylamino)phenyl]azo]-1H-imidazolium chloride,
- 1,3-dimethyl-2-[(4-aminophenyl)azo]-1H-imidazolium chloride, and
- 1-methyl-4-[(methylphenylhydrazono)methyl]-pyridinium methylsulphate.

Among the direct azo dyes, the following dyes may also be mentioned, described in COLOUR INDEX INTERNATIONAL 3rd edition:
- Disperse Red 17,
- Acid Yellow 9,
- Acid Black 1,
- Basic Red 22,
- Basic Red 76,
- Basic Yellow 57,
- Basic Brown 16,
- Acid Yellow 36,
- Acid Orange 7,
- Acid Red 33,
- Acid Red 35,
- Basic Brown 17,
- Acid Yellow 23,
- Acid Orange 24, and
- Disperse Black 9.

Non-limiting mention may also be made of 1-(4'-aminodiphenylazo)-2-methyl-4-bis-(β-hydroxyethyl) aminobenzene and 4-hydroxy-3-(2-methoxyphenylazo)-1-naphthalene sulphonic acid.

Among the direct quinone dyes, non-limiting mention may be made of the following dyes:
- Disperse Red 15,
- Solvent Violet 13,
- Acid Violet 43,
- Disperse Violet 1,
- Disperse Violet 4,
- Disperse Blue 1,
- Disperse Violet 8,
- Disperse Blue 3,
- Disperse Red 11,
- Acid Blue 62,
- Disperse Blue 7,
- Basic Blue 22,
- Disperse Violet 15, and
- Basic Blue 99, as well as the following compounds:
- 1-N-methylmorpholiniumpropylamino-4-hydroxyanthraquinone,
- 1-aminopropylamino-4-methylaminoanthraquinone,
- 1-aminopropylaminoanthraquinone,
- 5-β-hydroxyethyl-1,4-diaminoanthraquinone,
- 2-aminoethylaminoanthraquinone, and
- 1,4-bis-(β,γ-dihydroxypropylamino)-anthraquinone.

Among the azine dyes, non-limiting mention may be made of the following compounds:
- Basic Blue 17 and
- Basic Red 2.

Among the triarylmethane dyes that can be used according to at least one embodiment of the present disclosure, non-limiting mention may be made of the following compounds:
- Basic Green 1,
- Acid Blue 9,
- Basic Violet 3,
- Basic Violet 14,
- Basic Blue 7,
- Acid Violet 49,
- Basic Blue 26, and
- Acid Blue 7.

Among the indoamino dyes that can be used according to the present disclosure, non-limiting mention may be made of the following compounds:
- 2-β-hydroxyethylamino-5-[bis-(β-4'-hydroxyethyl)amino]anilino-1,4-benzoquinone,
- 2-β-hydroxyethylamino-5-(2'-methoxy-4'-amino)anilino-1,4-benzoquinone,
- 3-N(2'-chloro-4'-hydroxy)phenyl-acetylamino-6-methoxy-1,4-benzoquinone imine,
- 3-N(3'-chloro-4'-methylamino)phenyl-ureido-6-methyl-1,4-benzoquinone imine, and
- 3-[4'-N-(ethyl,carbamylmethyl)-amino]-phenyl-ureido-6-methyl-1,4-benzoquinone imine.

Among the dyes of the tetraazapentamethine type that can be used according to the present disclosure, non-limiting mention may be made of the following compounds shown in the following table, An being defined as previously:

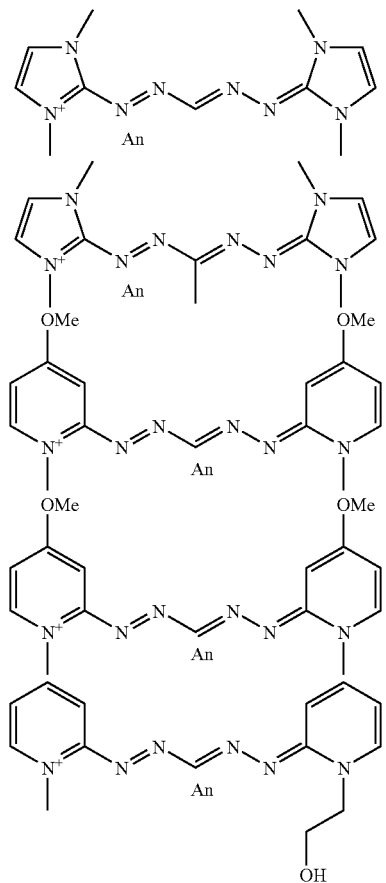

-continued

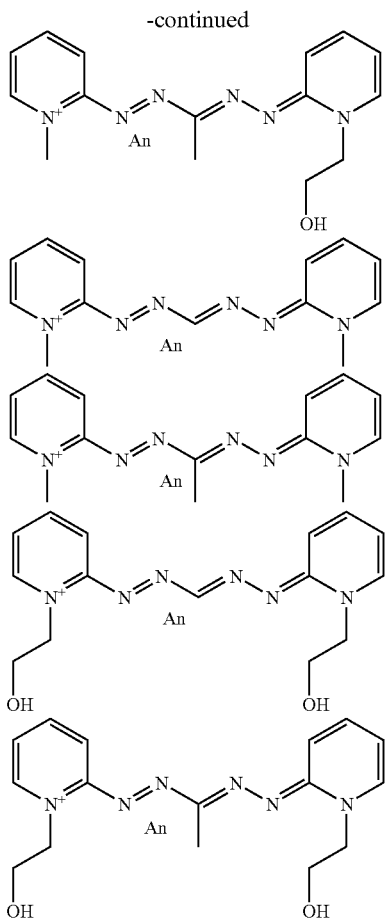

Among the natural direct dyes that can be used according to at least one embodiment of the disclosure, non-limiting mention may be made of lawsone, juglone, alizarin, purpurin, carminic acid, kermesic acid, purpurogallin, protocatechaldehyde, indigo, isatin, curcumine, spinulosine, and apigenidine. It is also possible to use extracts or decoctions containing these natural dyes and also henna-based cataplasms or extracts.

The direct dye or dyes different from those of formula (I) used in at least one embodiment are present in an amount ranging from 0.001 to 20 wt. % of the total weight of the composition, such as, for example, from 0.005 to 10 wt. %.

The composition according to at least one embodiment of the present disclosure can also contain at least one oxidizing agent conventionally used for the oxidation dyeing of keratin fibers, such as hydrogen peroxide, urea peroxide, alkali metal bromates, persalts such as perborates and persulphates, peracids and oxidase enzymes among which we may mention peroxidases, 2-electron oxido-reductases such as uricases and 4-electron oxygenases such as laccases. In at least one embodiment, hydrogen peroxide is used.

The medium suitable for dyeing, also called dyeing support, is a cosmetic medium that may comprise water or a mixture of water and at least one organic solvent for dissolving the compounds that would not be sufficiently soluble in water. As examples of organic solvents, non-limiting mention may be made of $C_1$-$C_4$ lower alkanols, such as ethanol and isopropanol; polyols and ethers of polyols such as 2-butoxyethanol, propyleneglycol, glycerol, monomethylether of propyleneglycol, monoethylether and monomethylether of diethyleneglycol, as well as aromatic alcohols such as benzyl alcohol or phenoxyethanol, and mixtures thereof.

In at least one embodiment of the present disclosure, the solvents are present in an amount ranging from 1 to 40 wt. % relative to the total weight of the dyeing composition, such as, for example, from 5 to 30 wt. %.

The dyeing composition according to at least one embodiment of the present disclosure can also contain various additives used conventionally in hair-dyeing compositions, such as anionic, cationic, non-ionic, amphoteric, zwitterionic surfactants or mixtures thereof, anionic, cationic, non-ionic, amphoteric, zwitterionic polymers or mixtures thereof, mineral or organic thickening agents, and, for example, anionic, cationic, non-ionic and amphoteric associative thickening agents, antioxidizing agents, penetrating agents, sequestering agents, perfumes, buffers, dispersants, conditioners such as volatile or non-volatile, modified or unmodified silicones, film-forming agents, ceramides, preservatives and opacifiers.

In at least one embodiment, the above additives are present in an amount for each of them ranging from 0.01 to 20 wt. % relative to the weight of the composition.

Of course, a person skilled in the art will ensure that any additional compound or compounds selected are such that the advantageous properties intrinsic to the dyeing composition according to the disclosure will not be adversely affected, or not substantially so, by any additions envisaged.

The pH of the dyeing composition according to at least one embodiment of the present disclosure ranges from 3 to 12, such as, for example, from 5 to 11 or from 6 to 10.5. The pH can be adjusted to the desired value by means of acidifying or alkalizing agents usually employed in the dyeing of keratin fibers or alternatively by means of conventional buffer systems.

Among the acidifying agents that may be used, non-limiting mention may be made of the following examples: mineral or organic acids such as hydrochloric acid, orthophosphoric acid, sulphuric acid, carboxylic acids such as acetic acid, tartaric acid, citric acid, lactic acid, and sulphonic acids.

Among the alkalizing agents that may be used, non-limiting mention the following examples: ammonia, alkaline carbonates, alkanolamines, such as mono-, di- and triethanolamines as well as their derivatives, hydroxides of sodium or of potassium and compounds of the following formula (II):

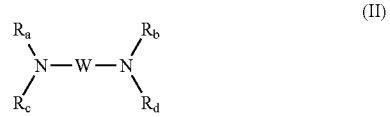

(II)

wherein W is a propylene residue optionally substituted with a hydroxyl group or a $C_1$-$C_4$ alkyl radical; $R_a$, $R_b$, $R_c$ and $R_d$, which may be identical or different, are chosen from hydrogen atoms, $C_1$-$C_4$ alkyl radicals and $C_1$-$C_4$ hydroxyalkyl radicals.

The dyeing composition according to the present disclosure can be in various forms, such as in the form of liquids, creams, gels, or in any other suitable form for carrying out the dyeing of keratin fibers, such as human hair.

The method of the present disclosure is a method in which the composition according to the present disclosure as defined previously is applied to the fibers, then the fibers are rinsed.

According to at least one embodiment, the composition of the disclosure is applied to keratin fibers in the presence of an oxidizing agent, and in this case it is called a highlighting dyeing. The oxidizing agent can be added to the composition of the present disclosure at the moment of use or it can be provided by an oxidizing composition containing it, applied simultaneously or sequentially with the composition of the present disclosure.

In at least one embodiment, the composition of the present disclosure contains at least one oxidation base.

The compositions, with or without oxidizing agent, are applied to the keratin materials and after a waiting time of 3 minutes to 1 hour, such as, for example, from 15 minutes to 45 minutes, the keratin fibers are rinsed, washed with shampoo, rinsed again and then dried.

The oxidizing composition can also contain various additives used conventionally in hair-dyeing compositions and as defined previously.

The pH of the oxidizing composition containing the oxidizing agent may be such that after mixing with the dyeing composition, the pH of the resulting composition applied to the keratin fibers ranges from 3 to 12, such as, for example, from 5 to 11 or from 6 to 10.5. The pH can be adjusted to the desired value by means of acidifying or alkalizing agents usually employed in the dyeing of keratin fibers and as defined previously.

The ready-to-use composition which is finally applied to the keratin fibers can be in various forms, such as in the form of liquids, creams, gels or in any other form suitable for carrying out the dyeing of keratin fibers, including human hair.

The present disclosure also relates to the use of the dyeing composition according to the present disclosure for the dyeing of keratin fibers.

The present disclosure also relates to a kit with several compartments or "dyeing kit," wherein a first compartment contains the dyeing composition according to the present disclosure and a second compartment contains an oxidizing agent. This kit can be equipped with means for supplying the desired mixture onto the hair, such as the kits described in French Patent No. FR-2 586 913.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical rangings and parameters setting forth the broad scope of the invention as approximations, the numerical values set forth in the specific examples are reported as precisely as possible. Any numerical value, however, inherently contains certain errors necessarily resulting from the standard deviation found in its respective testing measurement.

The following examples are intended to illustrate the invention. The invention is not, however, limited to these embodiments.

EXAMPLES

Examples of Preparations of Compounds According to the Present Disclosure

1) Example 1 by Route A

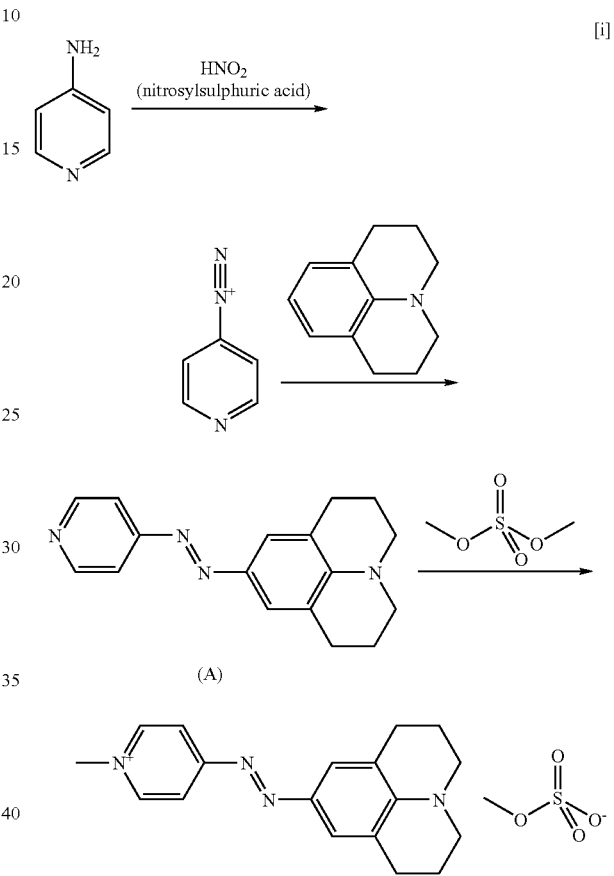

100 mL of anhydrous acetic acid and 500 mL of anhydrous propionic acid were added to 200 g of solution at 40% w/v of nitrosylsulphuric acid in sulphuric acid, the mixture was then cooled to below 5° C., and 50 g of 4-aminopyridine was added gradually. The mixture thus obtained was diluted by adding 200 mL of propionic acid and 40 mL of acetic acid, then a solution of 50 g of julolidine in 200 mL of methanol was added dropwise, keeping the temperature below 10° C. The reaction mixture was neutralized after 16 h of reaction at a temperature below 5° C. by introduction of 500 mL of water, 300 g of ice then 500 mL of 30% soda. The product (A) was extracted with ethyl acetate, and purified by chromatography on silica gel.

5 mL of dimethylsulphate was added to 5 g of pure product (A), diluted in 50 mL of dichloromethane, then the reaction mixture was stirred for 2 h. The mixture was concentrated by distillation of the solvents under vacuum, then the residue obtained was purified by dissolution in methyl ethyl ketone followed by precipitation with heptane. 7.12 g of a blue powder was obtained. Analyses indicated that it corresponded to the expected compound [i].

2) Example 2 by Route A

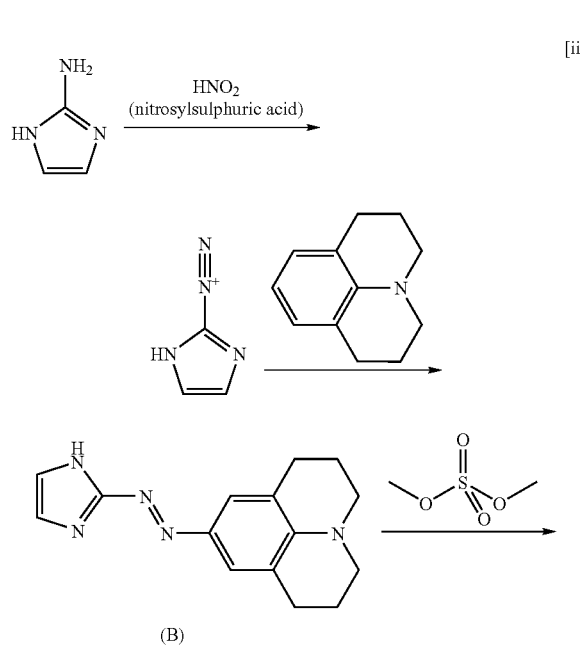

(B)

30 mL of 35% hydrochloric acid was added to 13.21 g of suspension of aminoimidazole in 100 mL of water, the mixture was cooled to −5° C. then a solution of 7 g of sodium nitrite in 10 mL of water was added dropwise, keeping the temperature below 0° C. Then 5 g of sulphanilic acid was added, the mixture was poured into an acid solution of julolidine obtained beforehand by mixing 8.75 g of julolidine, 175 mL of water and 225 mL of acetic acid and 40 g of sodium acetate, maintained at 0° C. After 2 h at 5° C., the reaction mixture was diluted, and adjusted to pH 8 with soda. The precipitated product (B) was filtered and washed with water.

5 g of (B) was dissolved in 50 mL of dichloromethane, and 5 mL of dimethylsulphate and 1.53 g of sodium acetate were added successively. After stirring for 2 h, the mixture was concentrated under vacuum, taken up in 100 mL of methyl ethyl ketone and then 100 mL of heptane was added. The precipitate obtained was washed with heptane, and 4.5 g of violet-black powder was obtained. After treatment with ion-exchange resin, the expected product [ii] was obtained in the form of hydrochloride (2.56 g). Analyses indicated that it corresponded to the expected compound [ii].

3) Example 3 by Route A

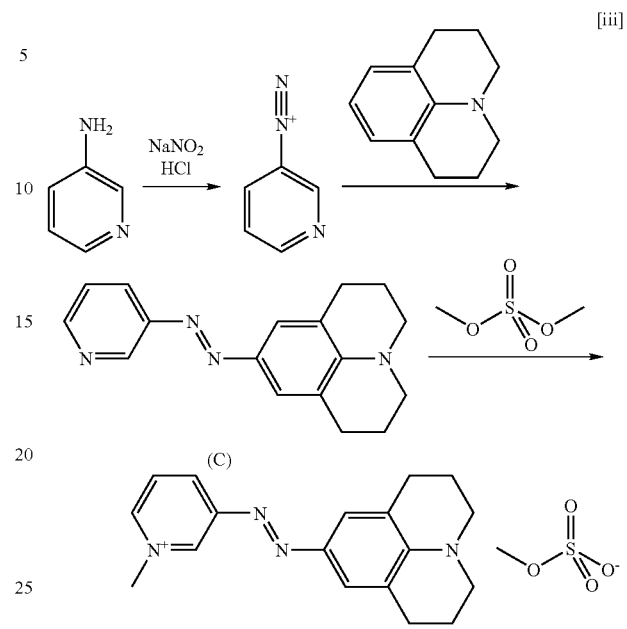

6.3 g of 3-aminopyridine, 17 mL of 35% hydrochloric acid and 65 g of ice were mixed in a 500-mL three-necked flask. A solution of 5.08 g of sodium nitrite in 20 mL of water was added dropwise, keeping the temperature of the mixture at 0° C. On completion of addition, the mixture was stirred for 20 min at 0° C. then a solution of 400 mg of urea in 10 mL of water was added. A solution of 11.6 g of julolidine in a mixture of ethanol (25 mL), 35% hydrochloric acid (16 mL) and ice (22 g) was added dropwise, keeping the temperature below 10° C. After 3 h at 5° C., the reaction mixture was neutralized by adding ammonia, until the pH was 9.5. The paste thus obtained was extracted with ethyl acetate with addition of water. The organic phase was dried and concentrated under vacuum; the product thus obtained was purified by chromatography (silica gel, eluent heptane/ethyl acetate) and a pure fraction of a powder of a deep red color was collected (4.3 g), corresponding to the expected compound (product (C)).

The product obtained in the above stage (127 mg) was dissolved in toluene (5 mL), 86 μL of dimethylsulphate was added and the reaction mixture was stirred for 72 h. The toluene was removed under vacuum, the product obtained was treated with water for 4 h at room temperature then dried under vacuum, obtaining a deep violet solid (170 mg). Analyses indicated that it corresponded to the expected compound [iii].

4) Example 4 by Route A

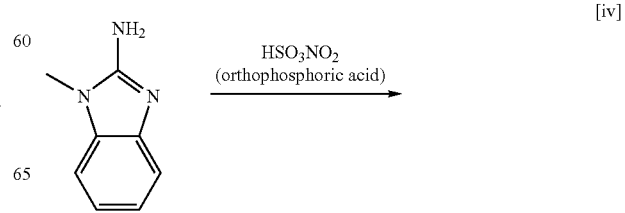

-continued

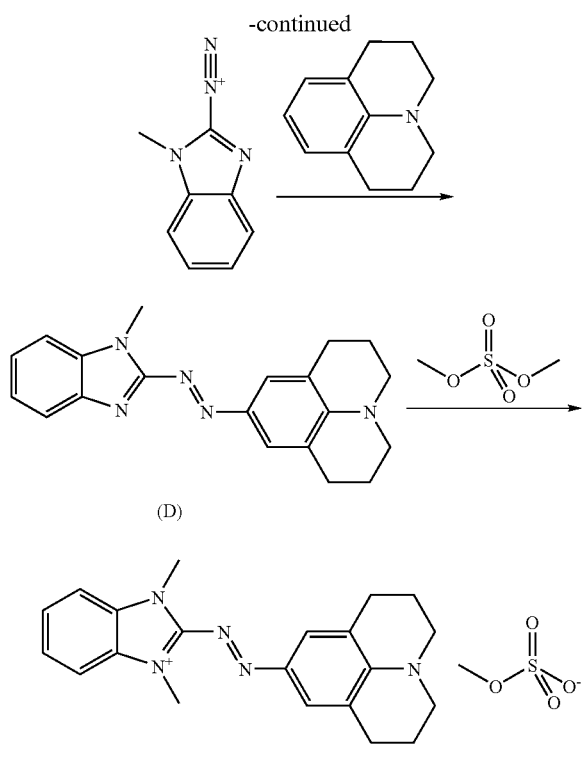

(D)

10 g of 2-amino-1-methyl benzimidazole was dissolved in a hot mixture of 60 ml of orthophosphoric acid and 20 ml of acetic acid.

26 g of nitrosylsulphuric acid (at 40% in sulphuric acid) was diluted in 25 mL of 98% phosphoric acid at 10° C. in a 250-mL three-necked flask equipped with a thermometer and an argon supply.

The first solution was poured dropwise into the second, maintaining the temperature between 2 and 5° C., in 30 min. The mixture was stirred for 15 min. 3.3 g of sulphamic acid was added and the mixture was stirred for 15 min.

13 g of julolidine, previously melted, was dissolved in 25 mL of DMF and 9 g of acetic acid.

The diazonium salt obtained in the preceding operation was poured dropwise into this solution, keeping the temperature below 10° C. The reaction mixture was diluted with 50 mL of water then kept at 0° C. for 18 h. 500 g of ice was added, then 100 mL of 30% soda; once more 500 g of ice and 150 mL of 30% soda. The mixture thus obtained was further diluted with 2 L of water then adjusted to pH 7 by adding sodium hydrogencarbonate (190 g).

The precipitate obtained was filtered (9.6 g) and dried. 1 g was purified by chromatography (silica, eluent dichloromethane/methanol). 100 mg of a red powder was obtained. Analyses indicated that it corresponded to the expected compound (D).

100 mg of D was dissolved in 20 mL of dichloromethane, and 500 μl of dimethyl sulphate was added dropwise to this mixture at room temperature. The solution was stirred for 5 min, then poured into 250 mL of ethyl ether. The precipitate was filtered and washed with 4×50 mL of ethyl ether. After drying, 50 mg of a black paste was recovered. Analyses indicated that it corresponded to the expected compound [iv].

5) Example 5 by Route A

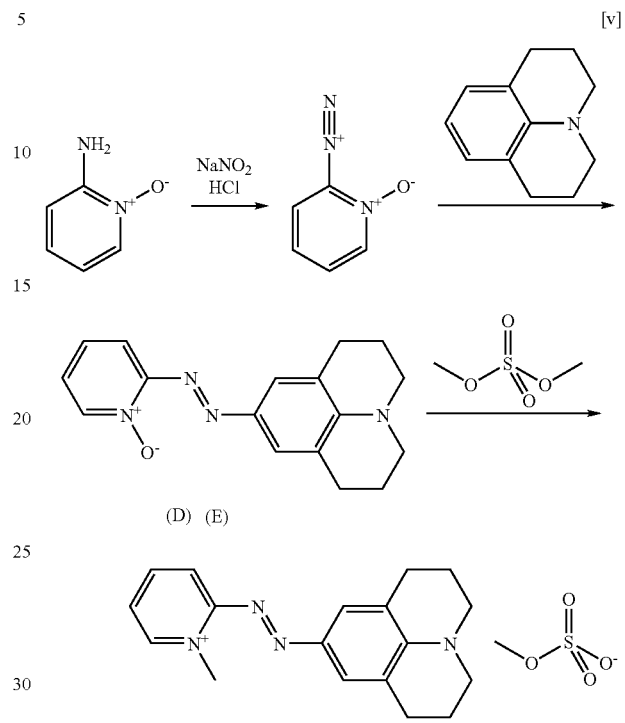

[v]

(D) (E)

11.8 g of julolidine was dissolved at 40° C. in 100 mL of water to which 5.7 mL of 35% hydrochloric acid had been added. 10 g of pyridine-2-amine 1-oxide (prepared according to the methods described in Synth. Commun. 1977, 509-514) was dissolved in 100 mL of water to which 17.4 mL of 35% hydrochloric acid had been added. A solution of 4.7 g of sodium nitrite dissolved in 10 mL of water was added, maintaining the temperature of the mixture at 0° C. The mixture was stirred for 30 min at 0° C. It was then poured into the acidic solution of julolidine, keeping the temperature below 10° C. The mixture was returned to room temperature in two hours. Addition of 70 g of sodium acetate brought the pH of the mixture to 4.2. After extraction with dichloromethane, rinsing with water, drying over sodium sulphate, filtration, concentration under vacuum, trituration in ether, filtration of the powder obtained and drying under vacuum, 10 g of dark violet powder was collected. Analyses showed that it corresponded to the expected product (E), with minor impurities.

5 g of (E) was dissolved in 20 mL of N-methylpyrrolidinone (NMP) and the solution was heated to 60° C. 4.05 g of dimethylsulphate was added to the mixture. After 2 h 30 min the solution was cooled to room temperature. 50 mL of 20% ammonia solution was added. After 15 h at room temperature, the mixture was extracted with dichloromethane (2×100 mL), washed with water, dried and concentrated under vacuum. The dark blue oil obtained was washed twice with isopropyl ether, then triturated in a third fraction. After filtration, rinsing with ether and drying under vacuum, 2 g of brown powder was collected. Analyses showed that it corresponded to the expected product [v].

Examples of Dyeing (Non-Highlighting Conditions)

The dyeing compositions were prepared in the following proportions:

Solution 1

| | |
|---|---|
| Hydroxyethylcellulose Natrosol 250MR | 0.72 g |
| Alkyl C8/C10 (50:50) hydroxyethylcellulose CG110 | 5 g |
| Benzyl alcohol | 4 g |
| Polyethylene glycol 400 | 4 g |
| Water | qs 100 g |

Solution 2: BUFFER pH 9.5

| | |
|---|---|
| Ammonium chloride (NH$_4$Cl) | 5.4 g |
| Ammonia in sol. at 20% | qs pH 9.5 (approx. 4 mL) |
| Demineralized water | qs 100 mL |

Solution 3: BUFFER pH 7

| | |
|---|---|
| KH$_2$PO$_4$ | 0.026 mol/L |
| Na$_2$PO$_4$ | 0.041 mol/L |
| Demineralized water | qs 500 mL |

The dyeing compositions were obtained by dissolving the dye stated below ($5\times10^{-3}$ mol/L) in solution 1, then adding an equivalent volume of buffer solution 2 or 3 (pH 7 or 9.5).

Each composition was applied to grey hair with 90% white, (1 g of hair to 6 g of solution). After a waiting time of 30 min, the locks of hair were rinsed, washed with a standard shampoo, rinsed again and then dried.

The following results of dyeing were obtained:

| | pH 7 | pH 9.5 |
|---|---|---|
| Dye [i] | Vivid chromatic blue | Vivid chromatic blue |
| Dye [ii] | Vivid chromatic violet | Vivid chromatic violet |
| Dye [iii] | Vivid chromatic fuchsia | Vivid chromatic fuchsia |
| Dye [iv] | Vivid chromatic blue | Vivid chromatic blue |
| Dye [v] | Vivid Blue-violet | Vivid Blue-violet |

Examples of Dyeing (Highlighting Conditions)

The dyeing compositions were prepared in the following proportions:

| | |
|---|---|
| Dye | 0.25 g |
| Hydroxyethylcellulose Natrosol 250MR | 0.72 g |
| Alkyl C8/C10 (50:50) hydroxyethylcellulose CG110 | 5 g |
| Benzyl alcohol | 4 g |
| Polyethylene glycol 400 | 4 g |
| Ammonium hydroxide | 13 g |
| Water | qs 100 g |

At the moment of use, this formulation was mixed weight for weight with 40 vol. % hydrogen peroxide solution then applied to locks of hair NW (Natural White) and PW (Permanent White)-1 g of hair to 6 g of solution. After waiting 30 min, the locks of hair were rinsed, washed with a standard shampoo, rinsed again and then dried.

The following results of dyeing were obtained

| | NW | PW |
|---|---|---|
| Dye [i] | Vivid chromatic blue | Vivid chromatic blue |
| Dye [ii] | Vivid chromatic violet | Vivid chromatic violet |

The dyed locks of hair were tested for resistance to washing, by carrying out 12 shampooings (with a standard shampoo) and assessing the color after these 12 shampooings. After 12 shampooings, the locks of hair were still colored.

What is claimed is:

1. A method for dyeing keratin fibers, comprising:
    applying to the keratin fibers a dyeing composition comprising at least one direct dye chosen from cationic azo compounds with a julolidine unit of formula (I):

$$A-N=N-\text{[julolidine with }(X)_x, (Y)_y, (Z)_z\text{ substituents]} \tag{I}$$

wherein:

A is a cationic aromatic heterocycle chosen from compounds of formulae (IIa), (IIb), and (IIc):

$$\text{(IIa): imidazolium ring with } R_1, R_1, (R_2)_e, a$$

$$\text{(IIb): pyridinium ring with } R_1, (R_2)_m, a$$

$$\text{(IIc): ring with } R_1, (R_2)_p, Q, D, a$$

wherein:

R$_1$ is chosen from, independently of one another:
    linear and branched, saturated and unsaturated C$_1$-C$_{16}$ hydrocarbon chains, which optionally form at least one carbon ring with 3 to 7 ring members, optionally condensed with the aromatic ring, optionally substituted, optionally interrupted by at least one group chosen from heteroatom chosen from oxygen, nitrogen and sulphur, and carbonyl groups; wherein $R_1$ does not contain a nitro, nitroso, peroxide and diazo bond; and wherein $R_1$ is directly attached to the nitrogen atom, quaternized or not, of the heteroaromatic ring A by means of a carbon atom;

$R_2$ is chosen from, independently of one another:
  linear and branched, saturated and unsaturated $C_1$-$C_{16}$ hydrocarbon chains, which optionally form at least one aromatic or non-aromatic carbon ring, with 3 to 6 ring members, optionally substituted, optionally interrupted by at least one heteroatom or by at least one group bearing at least one heteroatom;
  hydroxyl groups;
  $C_1$-$C_4$ alkoxy groups;
  $C_2$-$C_4$ (poly)hydroxyalkoxy groups;
  alkoxycarbonyl groups, $R_{11}O$—$CO$—, wherein $R_{11}$ is chosen from $C_1$-$C_4$ alkyl radicals;
  alkylcarbonyloxy radicals, $R_{12}CO$—$O$—, wherein $R_{12}$ is chosen from $C_1$-$C_4$ alkyl radicals;
  amino groups and amino groups substituted with one or two $C_1$-$C_4$ alkyl radicals, which may be identical or different, optionally bearing at least one hydroxyl group, wherein the two alkyl radicals optionally form, with the nitrogen atom to which they are attached, a heterocycle with 5 or 6 ring members optionally bearing another heteroatom identical to or different from nitrogen;
  alkylcarbonylamino groups, $R_{13}CO$—$NR_{13}$— and $R_{13}CO$—$NH$—, wherein the radicals $R_{13}$, independently of one another, are chosen from $C_1$-$C_4$ alkyl radicals;
  carbamoyl groups, $(R_{14})_2N$—$CO$, wherein the radicals $R_{14}$, independently of one another, which may be identical or different, are chosen from hydrogen atoms and $C_1$-$C_4$ alkyl radicals;
  ureido groups, $(R_{15})_2N$—$CO$—$NR_{16}$—, wherein the radicals $R_{15}$ and $R_{16}$, independently of one another, are chosen from hydrogen atoms and $C_1$-$C_4$ alkyl radicals;
  sulphonamide groups, $(R_{17})_2N$—$SO_2$—, wherein the radicals $R_{17}$, independently of one another, are chosen from hydrogen atoms and $C_1$-$C_4$ alkyl radicals;
  alkylsulphonylamino groups, $R_{18}SO_2$—$NR_{19}$—, wherein the radicals $R_{18}$ and $R_{19}$, independently of one another, are chosen from hydrogen atoms and $C_1$-$C_4$ alkyl radicals;
  guanidinium groups, $(R_{20})_2N$—$C(=NH_2+)$—$NR_{21}$-, wherein the radicals $R_{20}$ and $R_{21}$, independently of one another, are chosen from hydrogen atoms and $C_1$-$C_4$ alkyl radicals;
  nitro groups;
  cyano groups;
  halogen atoms;
wherein two radicals $R_2$, carried by adjacent carbon atoms optionally form, together with the carbon atom to which each is attached, an aromatic or non-aromatic condensed ring;

m is an integer ranging from 0 to 4;
e is an integer ranging from 0 to 2;
p is an integer ranging from 0 to 1;
D is chosen from groups $CR_2$ and nitrogen atoms;
Q is chosen from groups $NR_1$ and atoms of oxygen and sulphur;

bond a from formulae (IIa), (IIb) or (IIc), joins group A to the azo group;
when two radicals $R_2$ carried by two adjacent carbon atoms form an aromatic ring, bond a optionally joins group A to the azo group via said aromatic ring;
wherein the electroneutrality of the compounds is provided by at least one anion $An^-$, which may be identical or different, and is cosmetically acceptable;
X, Y and Z are optional substituents on the alkyl and aryl rings of the three-ring nucleus;
x is an integer ranging from 0 to 2;
y is an integer ranging from 0 to 6; and
z is an integer ranging from 0 to 6;
or their addition salts or their solvates,
wherein, in the definitions above, when an alkyl radical or the alkyl part of a radical is substituted, said substituted alkyl comprises at least one substituent chosen from:
  hydroxyl groups,
  $C_1$-$C_4$ alkoxy groups and $C_2$-$C_4$ (poly)hydroxyalkoxy groups,
  amino groups and amino groups substituted with at least one $C_1$-$C_4$ alkyl group, which may be identical or different, optionally bearing at least one hydroxyl group, and said alkyl radicals can form, with the nitrogen atom to which they are attached, a heterocycle with 5 or 6 ring members, optionally containing at least one other heteroatom which may or may not be nitrogen;
wherein, in the definitions above, when an aryl or heteroaryl radical or the aryl or heteroaryl part of a radical is substituted, said substituted aryl or heteroaryl comprises at least one substituent carried by a carbon atom, wherein for the aromatic ring of the three ring nucleus of said julolidine unit said substituent is X, and wherein X or said at least one substituent is chosen from:
  $C_1$-$C_{16}$ alkyl radicals, optionally substituted with at least one radical chosen from hydroxy, $C_1$-$C_2$ alkoxy, $C_2$-$C_4$ (poly)-hydroxyalkoxy, acylamino, amino substituted with one or two $C_1$-$C_4$ alkyl radicals, which may be identical or different, optionally bearing at least one hydroxyl group, or the two radicals can form, with the nitrogen atom to which they are attached, a heterocycle with 5 or 7 ring members, optionally containing another heteroatom identical to or different from nitrogen;
  halogen atoms;
  hydroxyl groups;
  $C_1$-$C_2$ alkoxy radicals;
  $C_2$-$C_4$ (poly)-hydroxyalkoxy radicals;
  amino radicals;
  amino radicals substituted with one or two $C_1$-$C_4$ alkyl radicals, which may be identical or different, optionally bearing at least one hydroxyl group;
  acylamino radicals, —$NR_{31}$—$COR_{32}$, wherein the radical $R_{31}$ is chosen from hydrogen atoms and $C_1$-$C_4$ alkyl radicals optionally bearing at least one hydroxyl group and the radical $R_{32}$ is chosen from $C_1$-$C_2$ alkyl radicals;
  carbamoyl radicals, $(R_{33})_2N$—$CO$—, wherein the radicals $R_{33}$, which may be identical or different, are chosen from hydrogen atoms and $C_1$-$C_4$ alkyl radicals optionally bearing at least one hydroxyl group;
  alkylsulphonylamino radicals, $R_{34}SO_2$—$NR_{35}$—, wherein the radical $R_{34}$ is chosen from hydrogen atoms and $C_1$-$C_4$ alkyl radicals optionally bearing at least one hydroxyl group, and the radical $R_{35}$ is chosen from $C_1$-$C_4$ alkyl radicals and phenyl radicals;

aminosulphonyl radicals, $(R_{36})_2N—SO_2—$, wherein the radicals $R_{36}$, which may be identical or different, are chosen from hydrogen atoms and $C_1$-$C_4$ alkyl radicals optionally bearing at least one hydroxyl group;

wherein, in the definitions above, when the cyclic or heterocyclic part of a non-aromatic radical is substituted, it comprises at least one substituent carried by a carbon atom, wherein for the non-aromatic rings of the three ring nucleus of said julolidine unit said substituents are Y and Z, and wherein Y and Z or said at least one substituent is chosen from:

hydroxyl groups, $C_1$-$C_4$ alkoxy and $C_2$-$C_4$ (poly)hydroxyalkoxy radicals, alkylcarbonylamino radicals, $(R_{41}CO—NR_{42}—$, wherein the radical $R_{42}$ is chosen from hydrogen atoms and $C_1$-$C_4$ alkyl radicals optionally bearing at least one hydroxyl group, and the radical $R_{41}$ is chosen from $C_1$-$C_2$ alkyl radicals and amino radicals substituted with two $C_1$-$C_4$ alkyl groups, which may be identical or different, optionally bearing at least one hydroxyl group, and said alkyl radicals can form, with the nitrogen atom to which they are attached, a heterocycle with 5 or 6 ring members, optionally containing at least one other heteroatom which may or may not be nitrogen;

wherein for all definitions above, when a ring does not carry the maximum number of substituents, the unsubstituted position or positions then carry a hydrogen atom.

2. The method according to claim 1, wherein $R_1$ is chosen from $C_1$-$C_8$ alkyl and hydroxyalkyl groups.

3. The method according to claim 1, wherein formulae (IIa), (IIb) and (IIc) comprise two radicals $R_2$ carried by adjacent carbon atoms, said radicals forming, together with the carbon atom to which each is attached, an aromatic condensed ring, optionally substituted.

4. The method according to claim 1, wherein e, m and p have the value 0.

5. The method according to claim 1, wherein x is 0, or x is 1 and X is chosen from alkyl, hydroxyl, hydroxyalkyl, alkoxy, amino, alkylamino, dialkylamino, and acylamino groups.

6. The method according to claim 1, wherein the compound of formula (I) is chosen from:

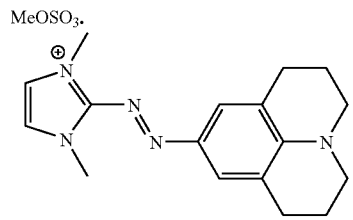

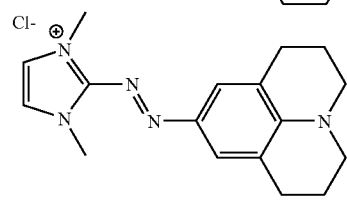

-continued

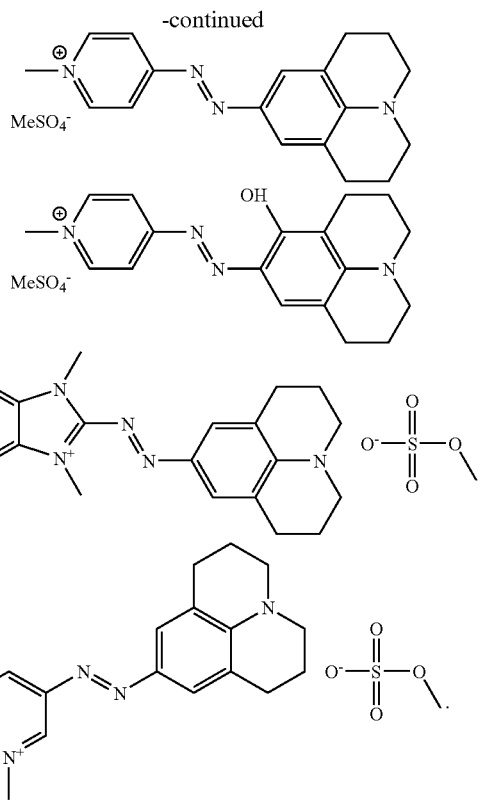

7. A method for dyeing keratin fibers, comprising:

applying to the keratin fibers a dyeing composition comprising at least one direct dye, leaving the composition on the keratin fibers for a waiting time ranging from 3 minutes to 1 hour; and rinsing the keratin fibers, wherein said direct dye is chosen from cationic azo compounds with a julolidine unit of formula (I):

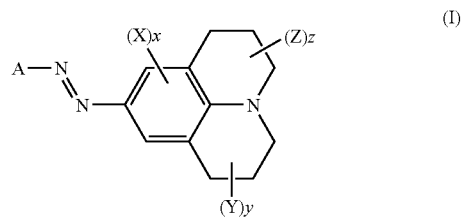

wherein:

A is a cationic aromatic heterocycle chosen from compounds of formulae (IIa), (IIb), and (IIc):

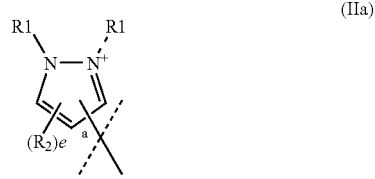

-continued

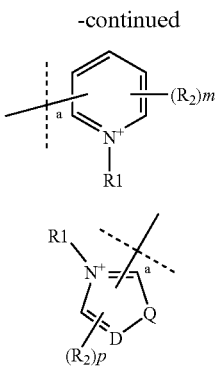

(IIb)

(IIc)

wherein:

R₁ is chosen from, independently of one another:
  linear and branched, saturated and unsaturated $C_1$-$C_{16}$ hydrocarbon chains, which optionally form at least one carbon ring with 3 to 7 ring members, optionally condensed with the aromatic ring, optionally substituted, optionally interrupted by at least one group chosen from heteroatom chosen from oxygen, nitrogen and sulphur, and carbonyl groups; wherein $R_1$ does not contain a nitro, nitroso, peroxide and diazo bond; and wherein $R_1$ is directly attached to the nitrogen atom, quaternized or not, of the heteroaromatic ring A by means of a carbon atom;

R₂ is chosen from, independently of one another:
  linear and branched, saturated and unsaturated $C_1$-$C_{16}$ hydrocarbon chains, which optionally form at least one aromatic or non-aromatic carbon ring, with 3 to 6 ring members, optionally substituted, optionally interrupted by at least one heteroatom or by at least one group bearing at least one heteroatom;
  hydroxyl groups;
  $C_1$-$C_4$ alkoxy groups;
  $C_2$-$C_4$ (poly)hydroxyalkoxy groups;
  alkoxycarbonyl groups, $R_{11}O$—CO—, wherein $R_{11}$ is chosen from $C_1$-$C_4$ alkyl radicals;
  alkylcarbonyloxy radicals, $R_{12}CO$—O—, wherein $R_{12}$ is chosen from $C_1$-$C_4$ alkyl radicals;
  amino groups and amino groups substituted with one or two $C_1$-$C_4$ alkyl radicals, which may be identical or different, optionally bearing at least one hydroxyl group, wherein the two alkyl radicals optionally form, with the nitrogen atom to which they are attached, a heterocycle with 5 or 6 ring members optionally bearing another heteroatom identical to or different from nitrogen;
  alkylcarbonylamino groups, $R_{13}CO$—$NR_{13}$— and $R_{13}CO$—NH—, wherein the radicals $R_{13}$, independently of one another, are chosen from $C_1$-$C_4$ alkyl radicals;
  carbamoyl groups, $(R_{14})_2N$—CO, wherein the radicals $R_{14}$, independently of one another, which may be identical or different, are chosen from hydrogen atoms and $C_1$-$C_4$ alkyl radicals;
  ureido groups, $(R_{15})_2N$—CO—$NR_{16}$—, wherein the radicals $R_{15}$ and $R_{16}$, independently of one another, are chosen from hydrogen atoms and $C_1$-$C_4$ alkyl radicals;
  sulphonamide groups, $(R_{17})_2N$—$SO_2$—, wherein the radicals $R_{17}$, independently of one another, are chosen from hydrogen atoms and $C_1$-$C_4$ alkyl radicals;
  alkylsulphonylamino groups, $R_{18}SO_2$—$NR_{19}$—, wherein the radicals $R_{18}$ and $R_{19}$, independently of one another, are chosen from hydrogen atoms and $C_1$-$C_4$ alkyl radicals;
  guanidinium groups, $(R_{20})_2N$—C(=$NH_2$+)—$NR_{21}$–, wherein the radicals $R_{20}$ and $R_{21}$, independently of one another, are chosen from hydrogen atoms and $C_1$-$C_4$ alkyl radicals;
  nitro groups;
  cyano groups;
  halogen atoms;
wherein two radicals $R_2$, carried by adjacent carbon atoms optionally form, together with the carbon atom to which each is attached, an aromatic or non-aromatic condensed ring;
m is an integer ranging from 0 to 4;
e is an integer ranging from 0 to 2;
p is an integer ranging from 0 to 1;
D is chosen from groups $CR_2$ and nitrogen atoms;
Q is chosen from groups $NR_1$ and atoms of oxygen and sulphur;
bond a from formulae (IIa), (IIb) or (IIc), joins group A to the azo group;
when two radicals $R_2$ carried by two adjacent carbon atoms form an aromatic ring, bond a optionally joins group A to the azo group via said aromatic ring;
wherein the electroneutrality of the compounds is provided by at least one anion $An^-$, which may be identical or different, and is cosmetically acceptable;
X, Y and Z are optional substituents on the alkyl and aryl rings of the three-ring nucleus;
x is an integer ranging from 0 to 2;
y is an integer ranging from 0 to 6; and
z is an integer ranging from 0 to 6;
or their addition salts or their solvates,
wherein, in the definitions above, when an alkyl radical or the alkyl part of a radical is substituted, said substituted alkyl comprises at least one substituent chosen from:
  hydroxyl groups,
  $C_1$-$C_4$ alkoxy groups and $C_2$-$C_4$ (poly)hydroxyalkoxy groups,
  amino groups and amino groups substituted with at least one $C_1$-$C_4$ alkyl group, which may be identical or different, optionally bearing at least one hydroxyl group, and said alkyl radicals can form, with the nitrogen atom to which they are attached, a heterocycle with 5 or 6 ring members, optionally containing at least one other heteroatom which may or may not be nitrogen;
wherein, in the definitions above, when an aryl or heteroaryl radical or the aryl or heteroaryl part of a radical is substituted, said substituted aryl or heteroaryl comprises at least one substituent carried by a carbon atom, wherein for the aromatic ring of the three ring nucleus of said julolidine unit said substituent is X, and wherein X or said at least one substituent is chosen from:
  $C_1$-$C_{16}$ alkyl radicals, optionally substituted with at least one radical chosen from hydroxy, $C_1$-$C_2$ alkoxy, $C_2$-$C_4$ (poly)-hydroxyalkoxy, acylamino, amino substituted with one or two $C_1$-$C_4$ alkyl radicals, which may be identical or different, optionally bearing at least one hydroxyl group, or the two radicals can form, with the nitrogen atom to which they are attached, a heterocycle with 5 or 7 ring members, optionally containing another heteroatom identical to or different from nitrogen;

halogen atoms;

hydroxyl groups;

$C_1$-$C_2$ alkoxy radicals;

$C_2$-$C_4$ (poly)-hydroxyalkoxy radicals;

amino radicals;

amino radicals substituted with one or two $C_1$-$C_4$ alkyl radicals, which may be identical or different, optionally bearing at least one hydroxyl group;

acylamino radicals, —$NR_{31}$—$COR_{32}$, wherein the radical $R_{31}$ is chosen from hydrogen atoms and $C_1$-$C_4$ alkyl radicals optionally bearing at least one hydroxyl group and the radical $R_{32}$ is chosen from $C_1$-$C_2$ alkyl radicals;

carbamoyl radicals, $(R_{33})_2N$—CO—, wherein the radicals $R_{33}$, which may be identical or different, are chosen from hydrogen atoms and $C_1$-$C_4$ alkyl radicals optionally bearing at least one hydroxyl group;

alkylsulphonylamino radicals, $R_{34}SO_2$—$NR_{35}$—, wherein the radical $R_{34}$ is chosen from hydrogen atoms and $C_1$-$C_4$ alkyl radicals optionally bearing at least one hydroxyl group, and the radical $R_{35}$ is chosen from $C_1$-$C_4$ alkyl radicals and phenyl radicals;

aminosulphonyl radicals, $(R_{36})_2N$—$SO_2$—, wherein the radicals $R_{36}$, which may be identical or different, are chosen from hydrogen atoms and $C_1$-$C_4$ alkyl radicals optionally bearing at least one hydroxyl group;

wherein, in the definitions above, when the cyclic or heterocyclic part of a non-aromatic radical is substituted, it comprises at least one substituent carried by a carbon atom, wherein for the non-aromatic rings of the three ring nucleus of said julolidine unit said substituents are Y and Z, and wherein Y and Z or said at least one substituent is chosen from:

hydroxyl groups, $C_1$-$C_4$ alkoxy and $C_2$-$C_4$ (poly)hydroxyalkoxy radicals, alkylcarbonylamino radicals, ($R_{41}$CO—$NR_{42}$—, wherein the radical $R_{42}$ is chosen from hydrogen atoms and $C_1$-$C_4$ alkyl radicals optionally bearing at least one hydroxyl group, and the radical $R_{41}$ is chosen from $C_1$-$C_2$ alkyl radicals and amino radicals substituted with two $C_1$-$C_4$ alkyl groups, which may be identical or different, optionally bearing at least one hydroxyl group, and said alkyl radicals can form, with the nitrogen atom to which they are attached, a heterocycle with 5 or 6 ring members, optionally containing at least one other heteroatom which may or may not be nitrogen;

wherein for all definitions above, when a ring does not carry the maximum number of substituents, the unsubstituted position or positions then carry a hydrogen atom.

8. The method according to claim 7, wherein the composition is left on the keratin fibers for a waiting time ranging from 15 minutes to 45 minutes.

9. A composition for dyeing keratin fibers comprising, in a suitable dyeing medium, at least one direct dye chosen from cationic azo compounds with a julolidine unit of formula (I):

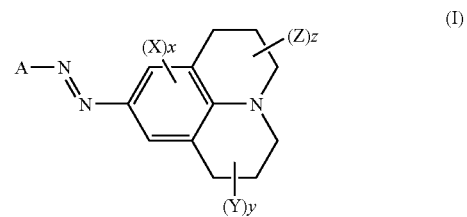

wherein:

A is a cationic aromatic heterocycle compound chosen from compounds of formulae (IIa), (IIb), and (IIc):

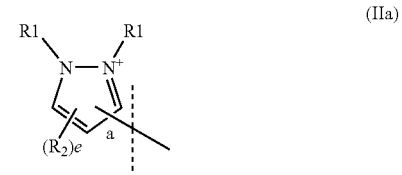

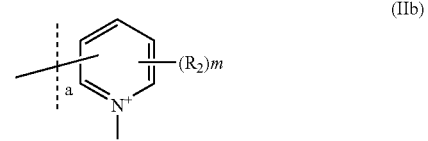

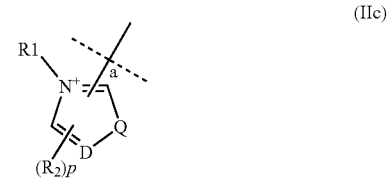

wherein:

$R_1$ is chosen from, independently of one another:

linear and branched, saturated and unsaturated $C_1$-$C_{16}$ hydrocarbon chains, which optionally form at least one carbon ring with 3 to 7 ring members, optionally condensed with the aromatic ring, optionally substituted, optionally interrupted by at least one group chosen from heteroatom chosen from oxygen, nitrogen and sulphur, and carbonyl groups; wherein $R_1$ does not contain a nitro, nitroso, peroxide and diazo bond; and wherein $R_1$ is directly attached to the nitrogen atom, quaternized or not, of the heteroaromatic ring A by means of a carbon atom;

$R_2$ is chosen from, independently of one another:

linear and branched, saturated and unsaturated $C_1$-$C_{16}$ hydrocarbon chains, which optionally form at least one aromatic or non-aromatic carbon ring, with 3 to 6 ring members, optionally substituted, optionally interrupted by at least one heteroatom or by at least one group bearing at least one heteroatom;

hydroxyl groups;

$C_1$-$C_4$ alkoxy groups;

$C_2$-$C_4$ (poly)hydroxyalkoxy groups;

alkoxycarbonyl groups, $R_{11}O$—CO—, wherein $R_{11}$ is chosen from $C_1$-$C_4$ alkyl radicals;

alkylcarbonyloxy radicals, $R_{12}CO$—O—, wherein $R_{12}$ is chosen from $C_1$-$C_4$ alkyl radicals;

amino groups and amino groups substituted with one or two $C_1$-$C_4$ alkyl radicals, which may be identical or different, optionally bearing at least one hydroxyl group, wherein the two alkyl radicals optionally form, with the nitrogen atom to which they are attached, a heterocycle with 5 or 6 ring members optionally bearing another heteroatom identical to or different from nitrogen;

alkylcarbonylamino groups, $R_{13}CO—NR_{13}—$ and $R_{13}CO—NH—$, wherein the radicals $R_{13}$, independently of one another, are chosen from $C_1$-$C_4$ alkyl radicals;

carbamoyl groups, $(R_{14})_2N—CO$, wherein the radicals $R_{14}$, independently of one another, which may be identical or different, are chosen from hydrogen atoms and $C_1$-$C_4$ alkyl radicals;

ureido groups, $(R_{15})_2N—CO—NR_{16}—$, wherein the radicals $R_{15}$ and $R_{16}$, independently of one another, are chosen from hydrogen atoms and $C_1$-$C_4$ alkyl radicals;

sulphonamide groups, $(R_{17})_2N—SO_2—$, wherein the radicals $R_{17}$, independently of one another, are chosen from hydrogen atoms and $C_1$-$C_4$ alkyl radicals;

alkylsulphonylamino groups, $R_{18}SO_2—NR_{19}—$, wherein the radicals $R_{18}$ and $R_{19}$, independently of one another, are chosen from hydrogen atoms and $C_1$-$C_4$ alkyl radicals;

guanidinium groups, $(R_{20})_2N—C(=NH_2+)—NR_{21}—$, wherein the radicals $R_{20}$ and $R_{21}$, independently of one another, are chosen from hydrogen atoms and $C_1$-$C_4$ alkyl radicals;

nitro groups;

cyano groups;

halogen atoms;

wherein two radicals $R_2$, carried by adjacent carbon atoms optionally form, together with the carbon atom to which each is attached, an aromatic or non-aromatic condensed ring;

m is an integer ranging from 0 to 4;

e is an integer ranging from 0 to 2;

p is an integer ranging from 0 to 1;

D is chosen from groups $CR_2$ and nitrogen atoms;

Q is chosen from groups $NR_1$ and atoms of oxygen and sulphur;

bond a from formulae (IIa), (IIb) or (IIc), joins group A to the azo group;

when two radicals $R_2$ carried by two adjacent carbon atoms form an aromatic ring, bond a optionally joins group A to the azo group via said aromatic ring;

wherein the electroneutrality of the compounds is provided by at least one anion $An^-$, which may be identical or different, and are cosmetically acceptable;

X, Y and Z are optional substituents on the alkyl and aryl rings of the three-ring nucleus;

x is an integer ranging from 0 to 2;

y is an integer ranging from 0 to 6; and z is an integer ranging from 0 to 6;

or their addition salts or their solvates, wherein, in the definitions above, when an alkyl radical or the alkyl part of a radical is substituted, said substituted alkyl comprises at least one substituent chosen from:

hydroxyl groups;

$C_1$-$C_4$ alkoxy groups and $C_2$-$C_4$ (poly)hydroxyalkoxy groups, amino groups and amino groups substituted with at least one $C_1$-$C_4$ alkyl group, which may be identical or different, optionally bearing at least one hydroxyl group, and said alkyl radicals can form, with the nitrogen atom to which they are attached, a heterocycle with 5 or 6 ring members, optionally containing at least one other heteroatom which may or may not be nitrogen;

wherein, in the definitions above, when an aryl or heteroaryl radical or the aryl or heteroaryl part of a radical is substituted, said substituted aryl or heteroaryl comprises at least one substituent carried by a carbon atom, wherein for the aromatic ring of the three ring nucleus of said julolidine unit said substituent is X, and wherein X or said at least one substituent is chosen from:

$C_1$-$C_{16}$ alkyl radicals, optionally substituted with at least one radical chosen from hydroxy, $C_1$-$C_2$ alkoxy, $C_2$-$C_4$ (poly)-hydroxyalkoxy, acylamino, amino substituted with one or two $C_1$-$C_4$ alkyl radicals, which may be identical or different, optionally bearing at least one hydroxyl group, or the two radicals can form, with the nitrogen atom to which they are attached, a heterocycle with 5 or 7 ring members, optionally containing another heteroatom identical to or different from nitrogen;

halogen atoms;

hydroxyl groups;

$C_1$-$C_2$ alkoxy radicals;

$C_2$-$C_4$ (poly)-hydroxyalkoxy radicals;

amino radicals;

amino radicals substituted with one or two $C_1$-$C_4$ alkyl radicals, which may be identical or different, optionally bearing at least one hydroxyl group;

acylamino radicals, $—NR_{31}—COR_{32}$, wherein the radical $R_{31}$ is chosen from hydrogen atoms and $C_1$-$C_4$ alkyl radicals optionally bearing at least one hydroxyl group and the radical $R_{32}$ is chosen from $C_1$-$C_2$ alkyl radicals;

carbamoyl radicals, $(R_{33})_2N—CO—$, wherein the radicals $R_{33}$, which may be identical or different, are chosen from hydrogen atoms and $C_1$-$C_4$ alkyl radicals optionally bearing at least one hydroxyl group;

alkylsulphonylamino radicals, $R_{34}SO_2—NR_{35}—$, wherein the radical $R_{34}$ is chosen from hydrogen atoms and $C_1$-$C_4$ alkyl radicals optionally bearing at least one hydroxyl group, and the radical $R_{35}$ is chosen from $C_1$-$C_4$ alkyl radicals and phenyl radicals;

aminosulphonyl radicals, $(R_{36})_2N—SO_2—$, wherein the radicals $R_{36}$, which may be identical or different, are chosen from hydrogen atoms and $C_1$-$C_4$ alkyl radicals optionally bearing at least one hydroxyl group;

wherein, in the definitions above, when the cyclic or heterocyclic part of a non-aromatic radical is substituted, it comprises at least one substituent carried by a carbon atom, wherein for the non-aromatic rings of the three ring nucleus of said julolidine unit said substituents are Y and Z, and wherein Y and Z or said at least one substituent is chosen from:

hydroxyl groups, $C_1$-$C_4$ alkoxy and $C_2$-$C_4$ (poly)hydroxyalkoxy radicals, alkylcarbonylamino radicals, $(R_{41}CO—NR_{42}—$, wherein the radical $R_{42}$ is chosen from hydrogen atoms and $C_1$-$C_4$ alkyl radicals optionally bearing at least one hydroxyl group, and the radical $R_{41}$ is chosen from $C_1$-$C_2$ alkyl radicals and amino radicals substituted with two $C_1$-$C_4$ alkyl groups, which may be identical or different, optionally bearing at least one hydroxyl group, and said alkyl radicals can form, with the nitrogen atom to which they are attached, a heterocycle with 5 or 6 ring members, optionally containing at least one other heteroatom which may or may not be nitrogen, wherein for all definitions above, when a ring does not carry the maximum number of substituents, the unsubstituted position or positions then carry a hydrogen atom.

10. The composition according to claim 9, wherein the at least one direct dye of formula (I) is present in an amount ranging from 0.001 to 20% by weight relative to the total weight of the composition.

11. The composition according to claim 10, wherein the at least one direct dye of formula (I) is present in an amount ranging from 0.01 to 10% by weight relative to the total weight of the composition.

12. The composition according to claim 9, further comprising at least one oxidation base chosen from para-phenylenediamines, bis-phenylalkylenediamines, para-aminophenols, ortho-aminophenols, heterocyclic bases and addition salts thereof.

13. The composition according to claim 12, wherein the at least one oxidation base is present in an amount ranging from 0.001 to 20% by weight relative to the total weight of the composition.

14. The composition according to claim 13, wherein the at least one oxidation base is present in an amount ranging from 0.005 to 6% by weight relative to the total weight of the composition.

15. The composition according to claim 9, further comprising at least one coupling agent chosen from meta-phenylenediamines, meta-aminophenols, meta-diphenols, naphthalenic coupling agents, heterocyclic coupling agents and addition salts thereof.

16. The composition according to claim 15, wherein the at least one coupling agent is chosen from 1,3-dihydroxy benzene, 1,3-dihydroxy 2-methyl benzene, 4-chloro 1,3-dihydroxy benzene, 2,4-diamino 1-(β-hydroxyethyloxy) benzene, 2-amino 4-(β-hydroxyethylamino) 1-methoxybenzene, 1,3-diamino benzene, 1,3-bis-(2,4-diaminophenoxy) propane, 3-ureido aniline, 3-ureido 1-dimethylamino benzene, sesamol, 1-β-hydroxyethylamino-3,4-methylenedioxybenzene, α-naphthol, 2-methyl-1-naphthol, 6-hydroxy indole, 4-hydroxy indole, 4-hydroxy N-methyl indole, 2-amino-3-hydroxy pyridine, 6-hydroxy benzomorpholine, 3,5-diamino-2,6-dimethoxypyridine, 1-N-(β-hydroxyethyl)amino-3,4-methylene dioxybenzene, 2,6-bis-(β-hydroxyethylamino)toluene and addition salts thereof.

17. The composition according to claim 15, wherein the at least one coupling agent is present in an amount ranging from 0.001 to 20% by weight relative to the total weight of the composition.

18. The composition according to claim 17, wherein the at least one coupling agent is present in an amount ranging from 0.005 to 6% by weight relative to the total weight of the composition.

19. The composition according to claim 9, further comprising at least one additional direct dye different from the compounds of formula (I), chosen from nitro dyes of the neutral, acid or cationic benzene series; neutral, acid or cationic direct azo dyes; quinone direct dyes; neutral, acid or cationic anthraquinone direct dyes; azine direct dyes; triarylmethane direct dyes; tetraazapentamethine direct dyes; indoamino direct dyes; and natural direct dyes.

20. The composition according to claim 19, wherein the at least one additional direct dye is present in an amount ranging from 0.001 and 20% by weight relative to the total weight of the composition.

21. The composition according to claim 20, wherein the at least one additional direct dye is present in an amount ranging from 0.005 to 10% by weight relative to the total weight of the composition.

22. The composition according to claim 9, further comprising at least one oxidizing agent chosen from hydrogen peroxide, urea peroxide, alkali metal bromates, persalts, peracids and oxidase enzymes.

23. The composition according to claim 22, wherein the at least one oxidizing agent is hydrogen peroxide.

24. The composition according to claim 9, further comprising at least one hydroxylated solvent.

25. The composition according to claim 24, wherein the at least one hydroxylated solvent is chosen from ethanol, propylene glycol, glycerol, and mono ethers of polyols.

26. The composition according to claim 9, further comprising at least one additive chosen from anionic, cationic, non-ionic, amphoteric, zwitterionic surfactants or mixtures thereof; anionic, cationic, non-ionic, amphoteric, zwitterionic polymers or mixtures thereof; mineral and organic thickening agents; antioxidizing agents; penetrating agents; sequestering agents; perfumes; buffers; dispersants; conditioners; film-forming agents; ceramides; preservatives and opacifiers.

27. The composition according to claim 26, wherein the at least one mineral and organic thickening agent is chosen from anionic, cationic, non-ionic and amphoteric associative polymeric thickening agents.

28. The composition according to claim 26, wherein the at least one conditioner is chosen from volatile and non-volatile, modified and unmodified silicones.

29. A kit comprising:
a first compartment comprising a composition comprising at least one direct dye, and
a second compartment comprising a composition comprising at least one oxidizing agent,
wherein said at least one direct dye is chosen from cationic azo compounds having a julolidine unit of formula (I):

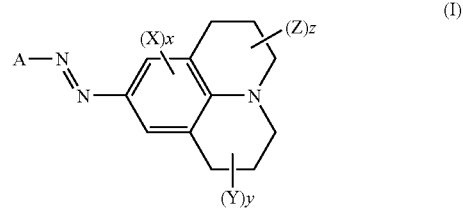

wherein:
A is a cationic aromatic heterocycle chosen from compounds of formulae (IIa), (IIb), and (IIc):

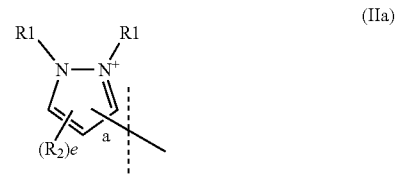

-continued

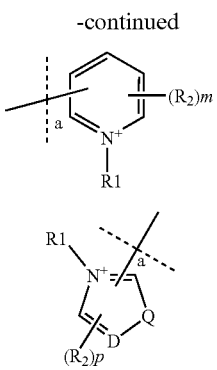

wherein:
R₁ is chosen from, independently of one another:
  linear and branched, saturated and unsaturated $C_1$-$C_{16}$ hydrocarbon chains, which optionally form at least one carbon ring with 3 to 7 ring members, optionally condensed with the aromatic ring, optionally substituted, optionally interrupted by at least one group chosen from heteroatom chosen from oxygen, nitrogen and sulphur, and carbonyl groups; wherein $R_1$ does not contain a nitro, nitroso, peroxide and diazo bond; and wherein $R_1$ is directly attached to the nitrogen atom, quaternized or not, of the heteroaromatic ring A by means of a carbon atom;

R₂ is chosen from, independently of one another:
  linear and branched, saturated and unsaturated $C_1$-$C_{16}$ hydrocarbon chains, which optionally form at least one aromatic or non-aromatic carbon ring, with 3 to 6 ring members, optionally substituted, optionally interrupted by at least one heteroatom or by at least one group bearing at least one heteroatom;
  hydroxyl groups;
  $C_1$-$C_4$ alkoxy groups;
  $C_2$-$C_4$ (poly)hydroxyalkoxy groups;
  alkoxycarbonyl groups, $R_{11}O$—CO—, wherein $R_{11}$ is chosen from $C_1$-$C_4$ alkyl radicals;
  alkylcarbonyloxy radicals, $R_{12}CO$—O—, wherein $R_{12}$ is chosen from $C_1$-$C_4$ alkyl radicals;
  amino groups and amino groups substituted with one or two $C_1$-$C_4$ alkyl radicals, which may be identical or different, optionally bearing at least one hydroxyl group, wherein the two alkyl radicals optionally form, with the nitrogen atom to which they are attached, a heterocycle with 5 or 6 ring members optionally bearing another heteroatom identical to or different from nitrogen;
  alkylcarbonylamino groups, $R_{13}CO$—$NR_{13}$— and $R_{13}CO$—NH—, wherein the radicals $R_{13}$, independently of one another, are chosen from $C_1$-$C_4$ alkyl radicals;
  carbamoyl groups, $(R_{14})_2N$—CO, wherein the radicals $R_{14}$, independently of one another, which may be identical or different, are chosen from hydrogen atoms and $C_1$-$C_4$ alkyl radicals;
  ureido groups, $(R_{15})_2N$—CO—$NR_{16}$—, wherein the radicals $R_{15}$ and $R_{16}$, independently of one another, are chosen from hydrogen atoms and $C_1$-$C_4$ alkyl radicals;
  sulphonamide groups, $(R_{17})_2N$—$SO_2$—, wherein the radicals $R_{17}$, independently of one another, are chosen from hydrogen atoms and $C_1$-$C_4$ alkyl radicals;
  alkylsulphonylamino groups, $R_{18}SO_2$—$NR_{19}$—, wherein the radicals $R_{18}$ and $R_{19}$, independently of one another, are chosen from hydrogen atoms and $C_1$-$C_4$ alkyl radicals;
  guanidinium groups, $(R_{20})_2N$—C(=$NH_2$+)—$NR_{21}$—, wherein the radicals $R_{20}$ and $R_{21}$, independently of one another, are chosen from hydrogen atoms and $C_1$-$C_4$ alkyl radicals;
  nitro groups;
  cyano groups;
  halogen atoms;
wherein two radicals $R_2$, carried by adjacent carbon atoms optionally form, together with the carbon atom to which each is attached, an aromatic or non-aromatic condensed ring;
m is an integer ranging from 0 to 4;
e is an integer ranging from 0 to 2;
p is an integer ranging from 0 to 1;
D is chosen from groups $CR_2$ and nitrogen atoms;
Q is chosen from groups $NR_1$ and atoms of oxygen and sulphur;
bond a from formulae (IIa), (IIb) or (IIc), joins group A to the azo group;
when two radicals $R_2$ carried by two adjacent carbon atoms form an aromatic ring, bond a optionally joins group A to the azo group via said aromatic ring;
wherein the electroneutrality of the compounds is provided by at least one anion $An^-$, which may be identical or different, and is cosmetically acceptable;
X, Y and Z are optional substituents on the alkyl and aryl rings of the three-ring nucleus;
x is an integer ranging from 0 to 2;
y is an integer ranging from 0 to 6; and
z is an integer ranging from 0 to 6;
or their addition salts or their solvates,
wherein, in the definitions above, when an alkyl radical or the alkyl part of a radical is substituted, said substituted alkyl comprises at least one substituent chosen from:
  hydroxyl groups,
  $C_1$-$C_4$ alkoxy groups and $C_2$-$C_4$ (poly)hydroxyalkoxy groups,
  amino groups and amino groups substituted with at least one $C_1$-$C_4$ alkyl group, which may be identical or different, optionally bearing at least one hydroxyl group, and said alkyl radicals can form, with the nitrogen atom to which they are attached, a heterocycle with 5 or 6 ring members, optionally containing at least one other heteroatom which may or may not be nitrogen;
wherein, in the definitions above, when an aryl or heteroaryl radical or the aryl or heteroaryl part of a radical is substituted, said substituted aryl or heteroaryl comprises at least one substituent carried by a carbon atom, wherein for the aromatic ring of the three ring nucleus of said julolidine unit said substituent is X, and wherein X or said at least one substituent is chosen from:
  $C_1$-$C_{16}$ alkyl radicals, optionally substituted with at least one radical chosen from hydroxy, $C_1$-$C_2$ alkoxy, $C_2$-$C_4$ (poly)-hydroxyalkoxy, acylamino, amino substituted with one or two $C_1$-$C_4$ alkyl radicals, which may be identical or different, optionally bearing at least one hydroxyl group, or the two radicals can form, with the nitrogen atom to which they are attached, a heterocycle with 5 or 7 ring members, optionally containing another heteroatom identical to or different from nitrogen;
  halogen atoms;

hydroxyl groups;

$C_1$-$C_2$ alkoxy radicals;

$C_2$-$C_4$ (poly)-hydroxyalkoxy radicals;

amino radicals;

amino radicals substituted with one or two $C_1$-$C_4$ alkyl radicals, which may be identical or different, optionally bearing at least one hydroxyl group;

acylamino radicals, —$NR_{31}$—$COR_{32}$, wherein the radical $R_{31}$ is chosen from hydrogen atoms and $C_1$-$C_4$ alkyl radicals optionally bearing at least one hydroxyl group and the radical $R_{32}$ is chosen from $C_1$-$C_2$ alkyl radicals;

carbamoyl radicals, $(R_{33})_2N$—CO—, wherein the radicals $R_{33}$, which may be identical or different, are chosen from hydrogen atoms and $C_1$-$C_4$ alkyl radicals optionally bearing at least one hydroxyl group;

alkylsulphonylamino radicals, $R_{34}SO_2$—$NR_{35}$—, wherein the radical $R_{34}$ is chosen from hydrogen atoms and $C_1$-$C_4$ alkyl radicals optionally bearing at least one hydroxyl group, and the radical $R_{35}$ is chosen from $C_1$-$C_4$ alkyl radicals and phenyl radicals;

aminosulphonyl radicals, $(R_{36})_2N$—$SO_2$—, wherein the radicals $R_{36}$, which may be identical or different, are chosen from hydrogen atoms and $C_1$-$C_4$ alkyl radicals optionally bearing at least one hydroxyl group;

wherein, in the definitions above, when the cyclic or heterocyclic part of a non-aromatic radical is substituted, it comprises at least one substituent carried by a carbon atom, wherein for the non-aromatic rings of the three ring nucleus of said julolidine unit said substituents are Y and Z, and wherein Y and Z or said at least one substituent is chosen from:

hydroxyl groups, $C_1$-$C_4$ alkoxy and $C_2$-$C_4$ (poly)hydroxyalkoxy radicals, alkylcarbonylamino radicals, ($R_{41}$CO—$NR_{42}$—, wherein the radical $R_{42}$ is chosen from hydrogen atoms and $C_1$-$C_4$ alkyl radicals optionally bearing at least one hydroxyl group, and the radical $R_{41}$ is chosen from $C_1$-$C_2$ alkyl radicals and amino radicals substituted with two $C_1$-$C_4$ alkyl groups, which may be identical or different, optionally bearing at least one hydroxyl group, and said alkyl radicals can form, with the nitrogen atom to which they are attached, a heterocycle with 5 or 6 ring members, optionally containing at least one other heteroatom which may or may not be nitrogen; and wherein for all definitions above, when a ring does not carry the maximum number of substituents, the unsubstituted position or positions then carry a hydrogen atom.

30. A cationic azo compound having a julolidine unit of formula (I):

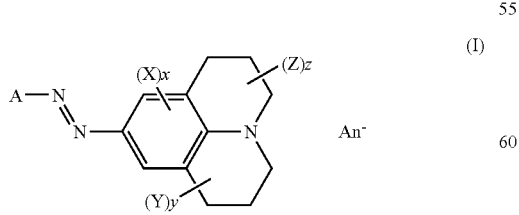

wherein:

A is a cationic aromatic heterocycle compound chosen from compounds of formulae (IIa), (IIb), and (IIc):

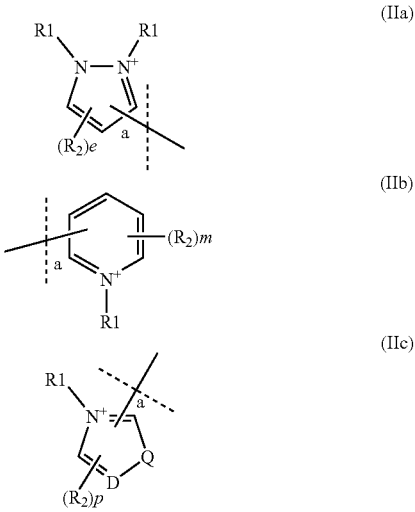

wherein:

$R_1$ is chosen from, independently of one another:

linear and branched, saturated and unsaturated $C_1$-$C_{16}$ hydrocarbon chains, which optionally form at least one carbon ring with 3 to 7 ring members, optionally condensed with the aromatic ring, optionally substituted, optionally interrupted by at least one group chosen from heteroatom chosen from oxygen, nitrogen and sulphur, and carbonyl groups; wherein $R_1$ does not contain a nitro, nitroso, peroxide and diazo bond; wherein $R_1$ is directly attached to the nitrogen atom, quaternized or not, of the heteroaromatic ring A by means of a carbon atom;

$R_2$ is chosen from, independently of one another:

linear and branched, saturated and unsaturated $C_1$-$C_{16}$ hydrocarbon chains, which optionally form at least one aromatic or non-aromatic carbon ring, with 3 to 6 ring members, optionally substituted, optionally interrupted by at least one heteroatom or by at least one group bearing at least one heteroatom;

hydroxyl groups;

$C_1$-$C_4$ alkoxy groups;

$C_2$-$C_4$ (poly)hydroxyalkoxy groups;

alkoxycarbonyl groups, $R_{11}O$—CO—, wherein $R_{11}$ is chosen from $C_1$-$C_4$ alkyl radicals;

alkylcarbonyloxy radicals, $R_{12}CO$—O—, wherein $R_{12}$ is chosen from $C_1$-$C_4$ alkyl radicals;

amino groups and amino groups substituted with one or two $C_1$-$C_4$ alkyl radicals, which may be identical or different, optionally bearing at least one hydroxyl group, wherein the two alkyl radicals optionally form, with the nitrogen atom to which they are attached, a heterocycle with 5 or 6 ring members optionally bearing another heteroatom identical to or different from nitrogen;

alkylcarbonylamino groups, $R_{13}CO$—$NR_{13}$— and $R_{13}CO$—NH—, wherein the radicals $R_{13}$, independently of one another, are chosen from $C_1$-$C_4$ alkyl radicals;

carbamoyl groups, $(R_{14})_2N$—CO, wherein the radicals $R_{14}$, independently of one another, which may be identical or different, are chosen from hydrogen atoms and $C_1$-$C_4$ alkyl radicals;

ureido groups, $(R_{15})_2N—CO—NR_{16}—$, wherein the radicals $R_{15}$ and $R_{16}$, independently of one another, are chosen from hydrogen atoms and $C_1$-$C_4$ alkyl radicals;

sulphonamide groups, $(R_{17})_2N—SO_2—$, wherein the radicals $R_{17}$, independently of one another, are chosen from hydrogen atoms and $C_1$-$C_4$ alkyl radicals;

alkylsulphonylamino groups, $R_{18}SO_2—NR_{19}—$, wherein the radicals $R_{18}$ and $R_{19}$, independently of one another, are chosen from hydrogen atoms and $C_1$-$C_4$ alkyl radicals;

guanidinium groups, $(R_{20})_2N—C(=NH_2+)—NR_{21}—$, wherein the radicals $R_{20}$ and $R_{21}$, independently of one another, are chosen from hydrogen atoms and $C_1$-$C_4$ alkyl radicals;

nitro groups;

cyano groups;

halogen atoms;

wherein two radicals $R_2$, carried by adjacent carbon atoms optionally form, together with the carbon atom to which each is attached, an aromatic or non-aromatic condensed ring;

m is an integer ranging from 0 to 4;

e is an integer ranging from 0 to 2;

p is an integer ranging from 0 to 1;

D is chosen from groups $CR_2$ and nitrogen atoms;

Q is chosen from groups $NR_1$ and atoms of oxygen and sulphur;

bond a from formulae (IIa), (IIb) or (IIc), joins group A to the azo group;

when two radicals $R_2$ carried by two adjacent carbon atoms form an aromatic ring, bond a optionally joins group A to the azo group via said aromatic ring;

wherein the electroneutrality of the compounds is provided by at least one anion $An^-$, which may be identical or different, and are cosmetically acceptable;

X, Y and Z are optional substituents on the alkyl and aryl rings of the three-ring nucleus;

x is an integer ranging from 0 to 2;

y is an integer ranging from 0 to 6; and z is an integer ranging from 0 to 6;

or their addition salts or their solvates, wherein, in the definitions above, when an alkyl radical or the alkyl part of a radical is substituted, said substituted alkyl comprises at least one substituent chosen from:

hydroxyl groups, $C_1$-$C_4$ alkoxy groups and $C_2$-$C_4$ (poly)hydroxyalkoxy groups, amino groups and amino groups substituted with at least one $C_1$-$C_4$ alkyl group, which may be identical or different, optionally bearing at least one hydroxyl group, and said alkyl radicals can form, with the nitrogen atom to which they are attached, a heterocycle with 5 or 6 ring members, optionally containing at least one other heteroatom which may or may not be nitrogen;

wherein, in the definitions above, when an aryl or heteroaryl radical or the aryl or heteroaryl part of a radical is substituted, said substituted aryl or heteroaryl comprises at least one substituent carried by a carbon atom, wherein for the aromatic ring of the three ring nucleus of said julolidine unit said substituent is X, and wherein X or said at least one substituent is chosen from:

$C_1$-$C_{16}$ alkyl radicals, optionally substituted with at least one radical chosen from hydroxy, $C_1$-$C_2$ alkoxy, $C_2$-$C_4$ (poly)-hydroxyalkoxy, acylamino, amino substituted with one or two $C_1$-$C_4$ alkyl radicals, which may be identical or different, optionally bearing at least one hydroxyl group, or the two radicals can form, with the nitrogen atom to which they are attached, a heterocycle with 5 or 7 ring members, optionally containing another heteroatom identical to or different from nitrogen;

halogen atoms;

hydroxyl groups;

$C_1$-$C_2$ alkoxy radicals;

$C_2$-$C_4$ (poly)-hydroxyalkoxy radicals;

amino radicals;

amino radicals substituted with one or two $C_1$-$C_4$ alkyl radicals, which may be identical or different, optionally bearing at least one hydroxyl group;

acylamino radicals, $—NR_{31}—COR_{32}$, wherein the radical $R_{31}$ is chosen from hydrogen atoms and $C_1$-$C_4$ alkyl radicals optionally bearing at least one hydroxyl group and the radical $R_{32}$ is chosen from $C_1$-$C_2$ alkyl radicals;

carbamoyl radicals, $(R_{33})_2N—CO—$, wherein the radicals $R_{33}$, which may be identical or different, are chosen from hydrogen atoms and $C_1$-$C_4$ alkyl radicals optionally bearing at least one hydroxyl group;

alkylsulphonylamino radicals, $R_{34}SO_2—NR_{35}—$, wherein the radical $R_{34}$ is chosen from hydrogen atoms and $C_1$-$C_4$ alkyl radicals optionally bearing at least one hydroxyl group, and the radical $R_{35}$ is chosen from $C_1$-$C_4$ alkyl radicals and phenyl radicals;

aminosulphonyl radicals, $(R_{36})_2N—SO_2—$, wherein the radicals $R_{36}$, which may be identical or different, are chosen from hydrogen atoms and $C_1$-$C_4$ alkyl radicals optionally bearing at least one hydroxyl group;

wherein, in the definitions above, when the cyclic or heterocyclic part of a non-aromatic radical is substituted, it comprises at least one substituent carried by a carbon atom, wherein for the non-aromatic rings of the three ring nucleus of said julolidine unit said substituents are Y and Z, and wherein Y and Z or said at least one substituent is chosen from:

hydroxyl groups, $C_1$-$C_4$ alkoxy and $C_2$-$C_4$ (poly)hydroxyalkoxy radicals, alkylcarbonylamino radicals, $(R_{41}CO—NR_{42}—$, wherein the radical $R_{42}$ is chosen from hydrogen atoms and $C_1$-$C_4$ alkyl radicals optionally bearing at least one hydroxyl group, and the radical $R_{41}$ is chosen from $C_1$-$C_2$ alkyl radicals and amino radicals substituted with two $C_1$-$C_4$ alkyl groups, which may be identical or different, optionally bearing at least one hydroxyl group, and said alkyl radicals can form, with the nitrogen atom to which they are attached, a heterocycle with 5 or 6 ring members, optionally containing at least one other heteroatom which may or may not be nitrogen; and wherein for all definitions above, when a ring does not carry the maximum number of substituents, the unsubstituted position or positions then carry a hydrogen atom, with the exception of 2-(9-julolidylazo)-3-methylbenzothiazolium perchlorate 2-(9-julolidylazo)-3-ethylthiazolium perchlorate.

31. The compound according to claim 30, wherein $R_1$ is chosen from $C_1$-$C_8$ alkyl and hydroxyalkyl groups.

32. The compound according to claim 30, wherein formulae (IIa), (IIb) and (IIc) comprise two radicals $R_2$ carried by adjacent carbon atoms, said radicals forming, together with the carbon atom to which each is attached, an aromatic condensed ring, optionally substituted.

33. The compound according to claim 30, wherein e, m and p have the value 0.
34. The compound according to claim 30, wherein x is 0, or x is 1 and X is chosen from alkyl, hydroxyl, hydroxyalkyl, alkoxy, amino, alkylamino, dialkylamino, and acylamino groups.
35. The compound according to claim 30, wherein the compound of formula (I) is chosen from:
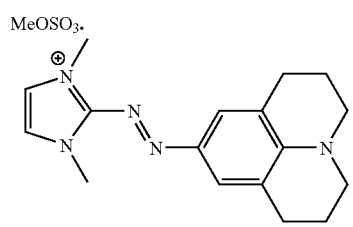
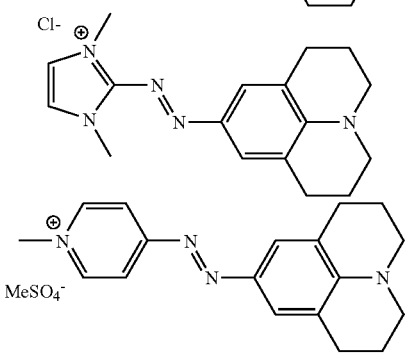
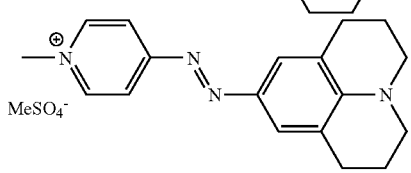
-continued
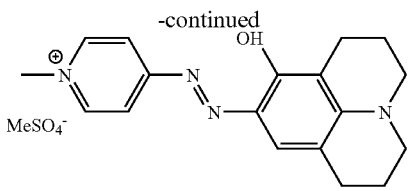
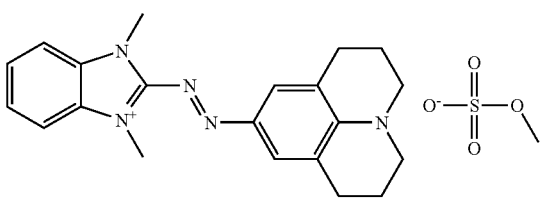
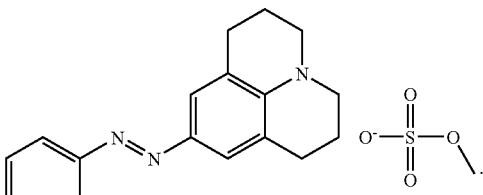
* * * * *

UNITED STATES PATENT AND TRADEMARK OFFICE
CERTIFICATE OF CORRECTION

PATENT NO. : 7,407,517 B2  Page 1 of 2
APPLICATION NO. : 11/508272
DATED : August 5, 2008
INVENTOR(S) : Daubresse et al.

It is certified that error appears in the above-identified patent and that said Letters Patent is hereby corrected as shown below:

In claim 6, column 33, lines 51-59,

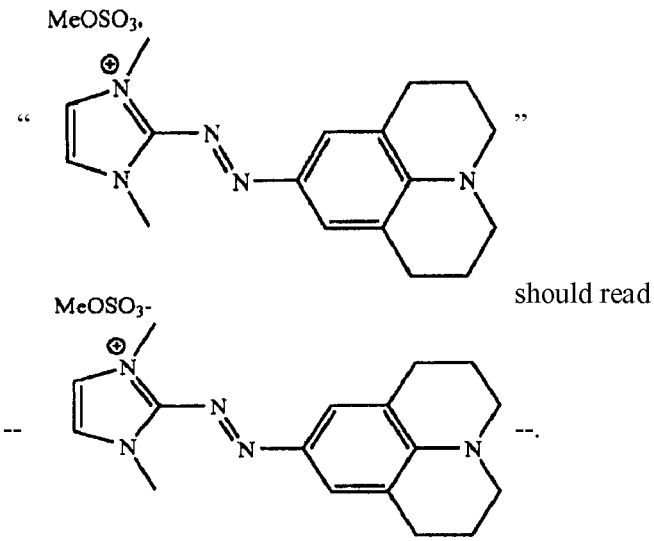

should read

UNITED STATES PATENT AND TRADEMARK OFFICE
CERTIFICATE OF CORRECTION

PATENT NO.         : 7,407,517 B2                                           Page 2 of 2
APPLICATION NO. : 11/508272
DATED              : August 5, 2008
INVENTOR(S)        : Daubresse et al.

It is certified that error appears in the above-identified patent and that said Letters Patent is hereby corrected as shown below:

In claim 35, column 49, lines 11-19,

" 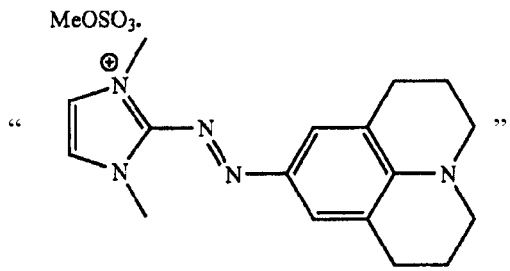 "

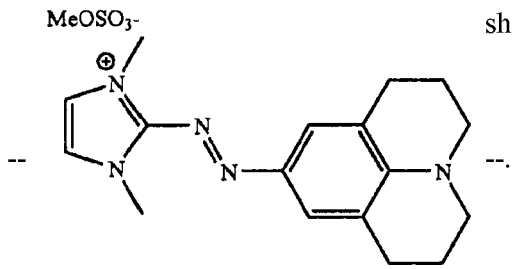 should read

--  --.

Signed and Sealed this

Thirtieth Day of September, 2008

JON W. DUDAS
*Director of the United States Patent and Trademark Office*